US009366580B2

(12) United States Patent
Hocker et al.

(10) Patent No.: US 9,366,580 B2
(45) Date of Patent: Jun. 14, 2016

(54) THERMAL MEASUREMENT AND PROCESS CONTROL

(71) Applicant: John Bean Technologies Corporation, Chicago, IL (US)

(72) Inventors: Jon A. Hocker, Bothell, WA (US); John R. Strong, Bellevue, WA (US); Ramesh M. Gunawardena, Chagrin Falls, OH (US); Richard D. Stockard, Kirkland, WA (US)

(73) Assignee: John Bean Technologies Corporation, Chicago, IL (US)

( * ) Notice: Subject to any disclaimer, the term of this patent is extended or adjusted under 35 U.S.C. 154(b) by 49 days.

(21) Appl. No.: 14/139,651

(22) Filed: Dec. 23, 2013

(65) Prior Publication Data

US 2014/0220193 A1     Aug. 7, 2014

(51) Int. Cl.

| | |
|---|---|
| *G01K 13/06* | (2006.01) |
| *G01K 13/00* | (2006.01) |
| *A22C 17/00* | (2006.01) |
| *G01N 33/12* | (2006.01) |
| *A23L 3/18* | (2006.01) |

(Continued)

(52) U.S. Cl.
CPC ............... *G01K 13/00* (2013.01); *A22C 17/008* (2013.01); *A23L 3/185* (2013.01); *G01K 13/06* (2013.01); *G01K 13/12* (2013.01); *G01N 33/02* (2013.01); *G01N 33/12* (2013.01); *B65G 47/53* (2013.01); *G01K 2207/06* (2013.01)

(58) Field of Classification Search
CPC ........ G01N 33/02–33/12; G01K 13/04–13/08; G01K 13/12; G01K 2207/00–2207/08; G01K 13/00; A22C 17/0073–17/008; A23L 3/185; B65G 47/53

USPC ........ 426/231–233; 99/328, 329 R, 333, 337, 99/338; 374/149, 155
See application file for complete search history.

(56) References Cited

U.S. PATENT DOCUMENTS

| | | | |
|---|---|---|---|
| 4,244,284 A | 1/1981 | Flavan, Jr. | |
| 4,990,347 A * | 2/1991 | Rasmussen | ............. A23L 3/003 426/231 |

(Continued)

FOREIGN PATENT DOCUMENTS

| | | |
|---|---|---|
| GB | 2 232 876 A | 1/1991 |
| JP | 2001-238614 A | 9/2001 |

OTHER PUBLICATIONS

International Search Report and Written Opinion mailed Jun. 4, 2014, issued in corresponding International Application No. PCT/US2013/077613, filed Dec. 23, 2013, 16 pages.

*Primary Examiner* — Drew Becker
(74) *Attorney, Agent, or Firm* — Christensen O'Connor Johnson Kindness PLLC

(57) ABSTRACT

A thermal processing and control system (300) includes a thermal processing station (312) for receiving food products (14) being carried on a conveyor system (316). A first scanning station (318) is located upstream from the thermal processing station (312) for scanning the food products being carried by the conveyor (316). An actuator (420) automatically connects temperature measuring devices (402) with selected food products (14). A diverter conveyor (324) diverts selected food products (14) from the conveyor (316) to a transverse conveyor (326) for either further processing or alternative processing, depending on how system (300) is configured. The temperature measuring devices (402) are automatically removed from the food products at station (329).

30 Claims, 13 Drawing Sheets

(51) Int. Cl.
   *G01K 13/12*   (2006.01)
   *G01N 33/02*   (2006.01)
   *B65G 47/53*   (2006.01)

(56) References Cited

U.S. PATENT DOCUMENTS

| | | | | |
|---|---|---|---|---|
| 5,082,373 | A * | 1/1992 | Rohde | A22B 5/0064 |
| | | | | 374/155 |
| 5,179,265 | A * | 1/1993 | Sheridan | A21B 1/245 |
| | | | | 219/388 |
| 5,253,564 | A * | 10/1993 | Rosenbrock | A21B 1/40 |
| | | | | 99/326 |
| 5,585,603 | A | 12/1996 | Vogeley, Jr. | |
| 5,668,634 | A * | 9/1997 | Newman | G01N 33/12 |
| | | | | 348/89 |
| 5,876,771 | A * | 3/1999 | Sizer | A23L 3/225 |
| | | | | 426/231 |
| 5,932,813 | A * | 8/1999 | Swartzel | G01K 3/04 |
| | | | | 374/E3.004 |
| 6,062,728 | A * | 5/2000 | Breunsbach | G01K 3/04 |
| | | | | 340/870.17 |
| 6,449,334 | B1 * | 9/2002 | Mazess | G01N 23/06 |
| | | | | 378/53 |
| 6,826,989 | B1 * | 12/2004 | Wattles | A22C 17/0093 |
| | | | | 83/102 |
| 6,866,417 | B2 * | 3/2005 | Gunawardena | G05D 23/1935 |
| | | | | 374/121 |
| 7,007,807 | B1 * | 3/2006 | Stockard | A21B 1/48 |
| | | | | 209/592 |
| 7,038,172 | B1 * | 5/2006 | Stuck | A47J 37/044 |
| | | | | 219/388 |
| 7,251,537 | B1 * | 7/2007 | Blaine | A22C 17/0086 |
| | | | | 452/156 |
| 7,712,662 | B2 * | 5/2010 | Rock | H04Q 9/00 |
| | | | | 235/375 |
| 9,016,458 | B2 * | 4/2015 | Bogle | B65G 15/42 |
| | | | | 198/341.07 |
| 9,041,799 | B2 | 5/2015 | Bielstein | |
| 2001/0041150 | A1 * | 11/2001 | Weng | A23L 3/027 |
| | | | | 422/3 |
| 2002/0004366 | A1 * | 1/2002 | Thorvaldsson | A22C 17/0093 |
| | | | | 452/198 |
| 2002/0044590 | A1 * | 4/2002 | Simunovic | G01K 1/022 |
| | | | | 374/176 |
| 2002/0054940 | A1 * | 5/2002 | Grose | A22B 7/007 |
| | | | | 426/231 |
| 2005/0287252 | A1 * | 12/2005 | Schrock | G01N 33/12 |
| | | | | 426/231 |
| 2007/0207242 | A1 * | 9/2007 | Carlsen | A22B 5/007 |
| | | | | 426/231 |
| 2008/0103723 | A1 * | 5/2008 | Burdett | G01K 1/02 |
| | | | | 702/130 |
| 2010/0008396 | A1 * | 1/2010 | Gaskins | G01J 5/0022 |
| | | | | 374/141 |
| 2010/0134620 | A1 | 6/2010 | Bielstein | |
| 2010/0179684 | A1 * | 7/2010 | Blaine | B07C 5/342 |
| | | | | 700/223 |
| 2012/0274470 | A1 * | 11/2012 | Sandvick | G01N 33/02 |
| | | | | 340/584 |
| 2013/0128919 | A1 * | 5/2013 | Austen | G01K 1/026 |
| | | | | 374/110 |
| 2013/0302483 | A1 | 11/2013 | Riefenstein | |
| 2014/0146849 | A1 * | 5/2014 | Randall | G01K 1/14 |
| | | | | 374/141 |
| 2014/0369383 | A1 * | 12/2014 | Yousef | G01K 3/14 |
| | | | | 374/137 |

* cited by examiner

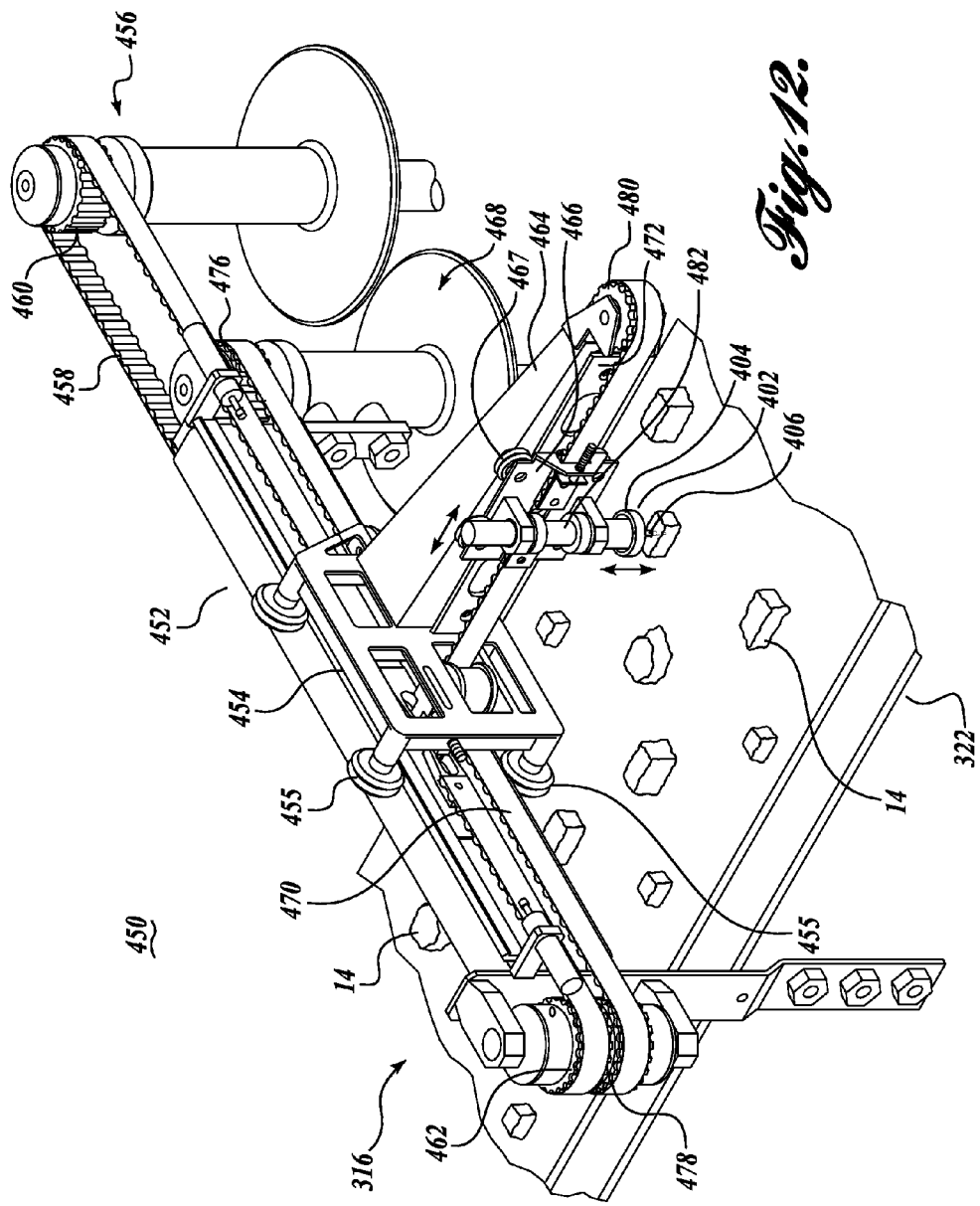

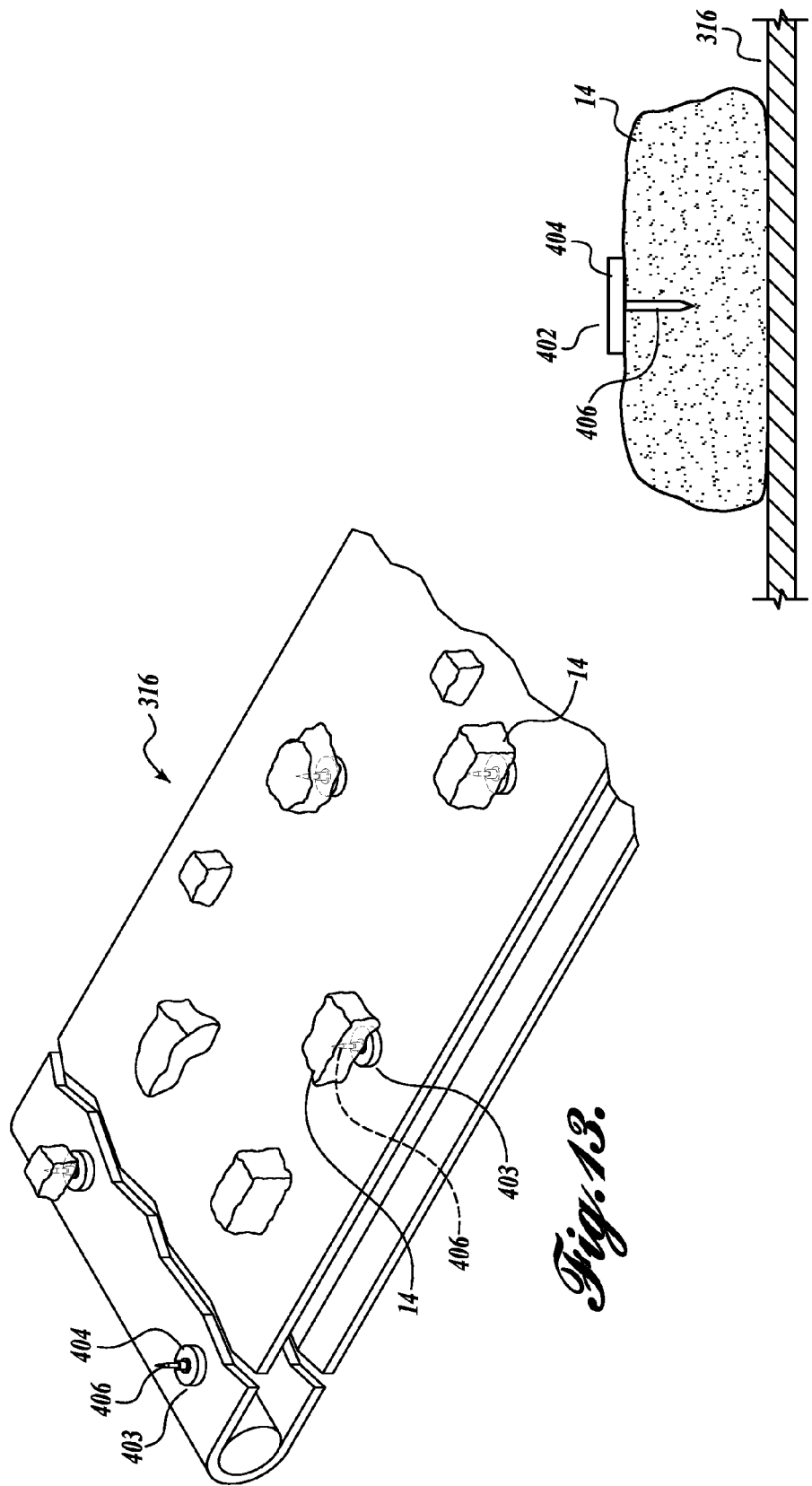

THERMAL MEASUREMENT AND PROCESS CONTROL

CROSS-REFERENCE TO RELATED APPLICATION

This application claims the benefit of U.S. Provisional Application No. 61/745,414, filed on Dec. 21, 2012, which is herein expressly incorporated by reference.

TECHNICAL FIELD

The present invention pertains to the thermal processing of work products, including particularly food products, and more specifically to measuring the temperature of thermally processed food products to determine the degree of thermal treatment applied to the food product, and making necessary adjustments to the thermal processing based on the results of the temperature measurements.

BACKGROUND

For obvious reasons, it is vitally important in the industrial food processing industry to fully cook food products prior to packaging. Such food products may not be subjected to any further step or process for killing bacteria prior to consumption of the food. Moreover, the performance of an industrial food processing system, such as an oven, fryer, steamer, roaster, chiller, or freezer can be significantly impacted by physical attributes of the food product, such as the thickness of the food product. Often, food product thickness can vary between batches or can trend thicker throughout a production shift without detection by personnel. If, for example, a new batch of food product enters a cooking process, and the average thickness of the new food product is larger than the thickness of the prior batch, it is desirable to proactively control the thermal process to insure proper cooking. Such proactive control is not widely practiced today. Typically, the control process is largely reactive. When an undercooked or otherwise under processed food product is detected as it leaves a thermal processing station, personnel typically respond by manually adjusting process settings.

The temperature of the food product leaving the thermal processing station is typically measured manually by inserting a thermal couple probe into the processed food product hopefully at or near the mass center of the workpiece. However, it is difficult for personnel to accurately determine where the mass center of the workpiece is located. An additional difficulty and source of temperature measurement error exists in placing the temperature probe at the estimated center of the workpiece even if the operator believes that he or she has identified the mass center. Moreover, a further source of error occurs when the measuring tip of the probe is positioned in what is thought to be the mass center of the workpiece, but in actuality is a void in the workpiece. A slight change in the position of a thermal probe can result in a significant difference in the temperature reading achieved, especially if the temperature probe is placed into a void in the workpiece.

Moreover, typically, the number of workpiece samples that are actually selected for temperature measurement is relatively small in relation to the number of workpieces being processed. Such relatively small sample size can be a source of temperature measurement error.

In an effort to reduce the likelihood of food products not being fully cooked or otherwise not sufficiently thermally processed, the current food industry practice is to adjust the cooking or other thermal process so that the center of the thickest workpieces reaches a desired temperature. Such desired temperature typically is a temperature at which pathogens are instantaneously killed from the temperature of the food product. However, typically the desired temperature is higher than such kill temperature so that there is a desired confidence level that all of the food products have reached a sufficient temperature. Thus, the temperature to be achieved may be increased to a desired temperature of perhaps several standard deviations above the actual kill temperature. This approach can result in a significant proportion of the workpieces being overly-cooked or otherwise overly-processed, which causes a decrease in yield as well as a decrease in profit because the overcooking or overthermal processing drives off moisture from the food product, resulting in a reduction in the weight of the processed food product as well as its quality. Applicants estimate that eliminating the overcooking in a single process line can result in an economic savings of hundreds of thousands of dollars per year. This economic benefit arises from not having to cook or otherwise thermally process based on the thickest, largest, or otherwise maximum or extreme food product in the population being processed. Other benefits include (1) a reduction in labor required to monitor, control, and report on the process, (2) a reduction in unscheduled sanitation procedures of the thermal processing system, including the thermal processing station and the conveyance systems removing the food product to and from the thermal processing station, as well as (3) increased production line operational time.

Because improperly or underthermally processed food products present a high safety risk, a highly hygienic solution is desired to ensure that the food products are fully cooked or otherwise fully thermally processed. As such, it is desirable to have minimal equipment situated over the food product traveling to a thermal processing station, during thermal processing at the thermal processing station, as well as traveling away from the thermal processing station, unless the equipment in question operates at a cooking temperature, or is otherwise maintained at a highly hygienic state. Complex equipment located over food product being thermally processed presents a contamination hazard since contaminated droplets of water or other moisture can fall on the cooked or otherwise processed food product.

In an effort to at least partially automate the temperature measurement function of cooked or otherwise processed food products, "pick-and-place" robots have been contemplated. The envisioned systems and equipment are situated over the food product stream, are used to remove selected food products from the food product stream and then transmit the food products to a temperature measurement location or station, where manual temperature measurement of the selected food product takes place. Concerns about this solution may have prevented pick-and-place systems from being reduced to practice for thermal processes.

An approach that is approved by food safety regulations as an alternative to simply reaching a minimum pathogen kill temperature in a food product is to achieve a required level of reduction of pathogens in the food product. Such pathogens can be killed over time, with the rate of kill depending on the temperature of the food product achieved. If the temperature profile of the food product over time is known, then the level of pathogen killed in the food product can be determined. If such temperature profile can be determined with accuracy, then the thermal processing time for the food product may be sufficiently tailored to the food product in question, rather than having to take the potentially less efficient strategy of ensuring that the thickest food product has been heated to above the instantaneous kill temperature of the pathogens in question.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure provides methods and systems for measuring the internal temperature of discrete, thermally treated workpieces, for example, food products, which include the steps of physically characterizing the workpieces while being conveyed on a conveyance system. Based on the physical characterization of the workpieces, sample workpieces are selected for temperature measurement. Next, temperature sensing devices are automatically functionally connected to the selected sample workpieces, with the temperature sensing devices travelling with the selected workpieces on the conveyance system. The temperatures sensed by the temperature sensing devices are monitored during the thermal processing of the selected sample workpieces. The temperature sensing data can be analyzed to determine the degree of thermal treatment that has occurred in the workpieces. This information can be used to determine if the workpieces have been adequately thermally processed, and also can be used to adjust the control parameters used during thermal processing of the workpieces.

In accordance with a further aspect of the present invention, wherein functionally interconnecting the temperature sensing devices with the selected sample workpieces includes inserting the temperature sensing devices into the selected sample workpieces.

In accordance with another aspect of the present invention, the temperature sensing devices are carried by the conveyance system, and the sample selected workpieces are placed over the temperature sensing devices.

In a further aspect of the present invention, the temperature sensing devices are inserted into the sample workpieces using a powered actuator system.

In accordance with a further aspect of the present invention, the level of thermal processing or treatment of the selected sample workpieces is determined by ascertaining if a threshold minimum temperature of the selected sample workpieces has been reached and/or determining the reduction in one or more selected bacteria resulting from the thermal processing of the selected sample workpieces.

In accordance with a further aspect of the present invention, based on a determined level of thermal processing of the selected sample workpieces that has occurred, selecting the manner of the subsequent processing of the workpieces. If the thermal processing of the selected sample workpieces has not been adequately performed, remedial action is taken with respect to the workpieces, conveyance system, and/or the manner of thermal processing of the workpieces.

In accordance with a further aspect of the present invention, the temperature profile of the workpieces is modeled to determine the extent of thermal processing of the workpieces independent of the temperature measurements using the temperature sensing devices, and optionally to verify the measured temperatures of the selected sample workpieces. Modeling can take into consideration one or more factors, including the type of workpiece, the density of the workpiece, the thickness range of the workpiece, the initial temperature of the workpiece, latent heat of the workpiece, the fat content of the workpiece, the moisture content of the workpiece, the level of loading of the workpiece on the conveyance system, the speed of the conveyance system, the time duration in which the workpieces are thermally processed, the temperature under which the workpieces are thermally processed, and/or the moisture conditions under which the workpieces are thermally processed.

In accordance with a further aspect of the present invention, a system for measuring the temperature of workpieces, for example, food products, processed at a thermal processing station under process parameters includes a conveyance system for conveying the food products in a stream through the processing station. A characterizing system physically characterizes all or some of the food products of the stream being carried by the conveyance system for a selection of sample food products for temperature measurement. An automatic system for automatically functionally connecting temperature sensing devices with the selected sample food products as the selected sample food products are carried by the conveyance system. A temperature monitoring device monitors the temperatures sensed by the temperature sensing devices.

In accordance with a further aspect of the present invention, a method is provided for processing a stream of food products in a thermal processing apparatus so that the food products have been sufficiently processed to meet regulatory requirements. The method includes scanning the food products to physically characterize the food products, and based on the results of the scanning of the food products, selecting sample food products for temperature measurement. Temperature sensing devices are automatically connected with the selected sample food products. The temperatures of the selected sample food products are monitored, including during the thermal processing of the selected sample food products. Based on the monitored temperatures of the selected sample food products, it is determined whether or not regulatory requirements for sufficient processing of the selected sample food products has occurred.

In accordance with a further aspect of the present invention, based on the scanning of the food products, one or more locations are selected on the sample food products at which to take temperature measurements.

In accordance with a further aspect of the present invention, the temperature rise in the food products is predicted over time during the thermal processing of the food products, and from such predicted temperature rise, a reduction in the level of selected bacteria during thermal processing of the food products is determined. Based on such predicted temperature rise in the selected food products, the operation of the thermal processing apparatus is controlled.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 12 is a fragmentary schematic view of an actuator of the present disclosure;

FIG. 13 is a fragmentary schematic view of an alternative arrangement of temperature measuring devices; and FIG. 14 is an enlarged schematic view of a temperature measuring device inserted into a sample food product.

DETAILED DESCRIPTION

In the Detailed Description, the reference to "food product" is to be understood to also refer to "food piece," "work product," or "workpiece."

The present application and claims relate to killing or eliminating pathogenic microorganisms that may be present on and/or in food products. The application also describes the killing of "bacteria" in and/or on food products. Such references to bacteria and pathogenic microorganisms relate to food pathogens, including, among others, the following: *E. coli, Salmonella* spp., *Clostridium botulinum, Staphylococcus aureus, Campylobacter jejuni, Yersinia enterocolitica* and *Yersinia pseudotuberculosis, Listeria monocytogenes, Vibrio cholerae* O1, *Vibrio cholerae* non-O1, *Vibrio parahaemolyticus* and other vibrios, *Vibrio vulnificus, Clostridium perfringens, Bacillus cereus, Aeromonas hydrophila* and other spp., *Plesiomonas shigelloides, Shigella* spp., miscellaneous enterics, and *Streptococcus*.

Figure 1:
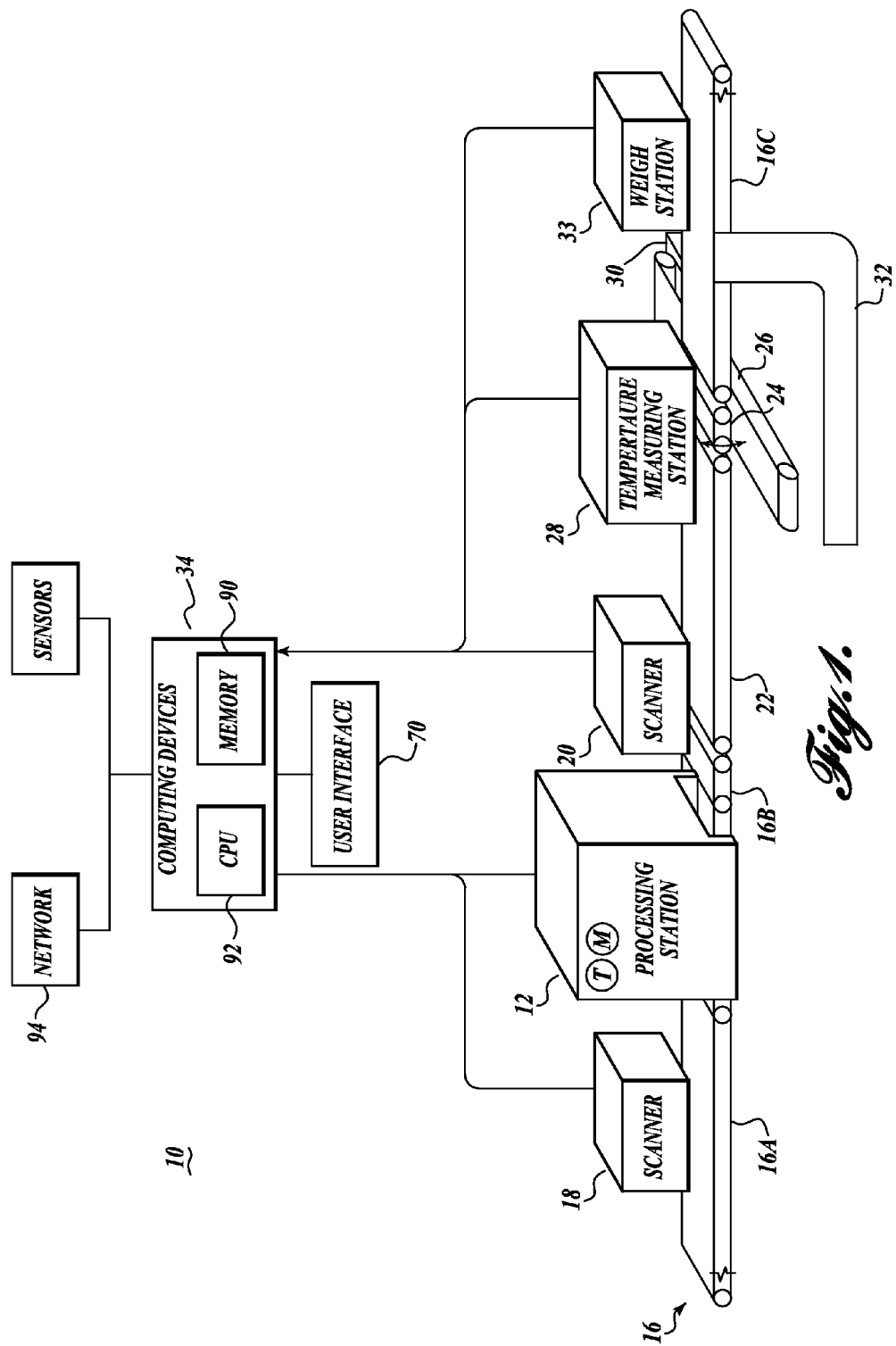
FIG. 1 is a schematic view of a thermal measurement process control system of the present disclosure.

Referring initially to FIG. 1, a thermal processing and control system 10 in accordance with the present disclosure includes a thermal processing station 12 for receiving work products, for example, in the form of food products 14 via the infeed section 16A of a conveyor system 16. The conveyor system 16 may itself travel through the thermal processing station 12, or the thermal processing station may have its own conveyor system(s). Upstream from thermal processing station 12, conveyor section 16A carries food products 14 past a first scanning station 18 for scanning the food products 14 being carried by the conveyor section 16A.

A second section 16B of conveyor 16 carries away food products 14 that have been processed at station 12. In this regard, food products are carried to a second scanning station 20 having its own conveyor section 22 positioned in registry with conveyor section 16B. See also FIGS. 2 and 3. The conveyor section 22 is also in registry with a diverter conveyor section 24 capable of diverting food products 14 to an underlying transverse conveyor 26. The transverse conveyor 26 is capable of positioning diverted food products at a temperature measurement station 28, whereat the temperature of the food product can be measured either manually or automatically. The transverse conveyor 26 is in registry with a receptacle 30 at the opposite end of the transverse conveyor from the location of the temperature measurement station 28. At the temperature measurement station, the transverse conveyor may be in registry with a return conveyor 32, that is capable of transporting the food product, after the temperature of the food product has been measured, back to the flow stream of conveyor 16, or to another desired location. An optional weighing station 33 is located downstream of this rejoinder location to weigh the food products 14 that proceed to the next processing station.

The system 10 also includes a computing device 34 that may be incorporated into either scanning station 18 or 20 or may be independent of such scanning station(s). The computing device is capable of receiving the scanning information from scanning stations 18 and 20, the temperature information from temperature measurement station 28, as well as receiving and sending information pertaining to the operation and control of a thermal processing station 12. As explained below, the information from the scanners as well as the temperature measurement station may be utilized to adjust and/or control the operation of the thermal processing station 12.

Figure 2:
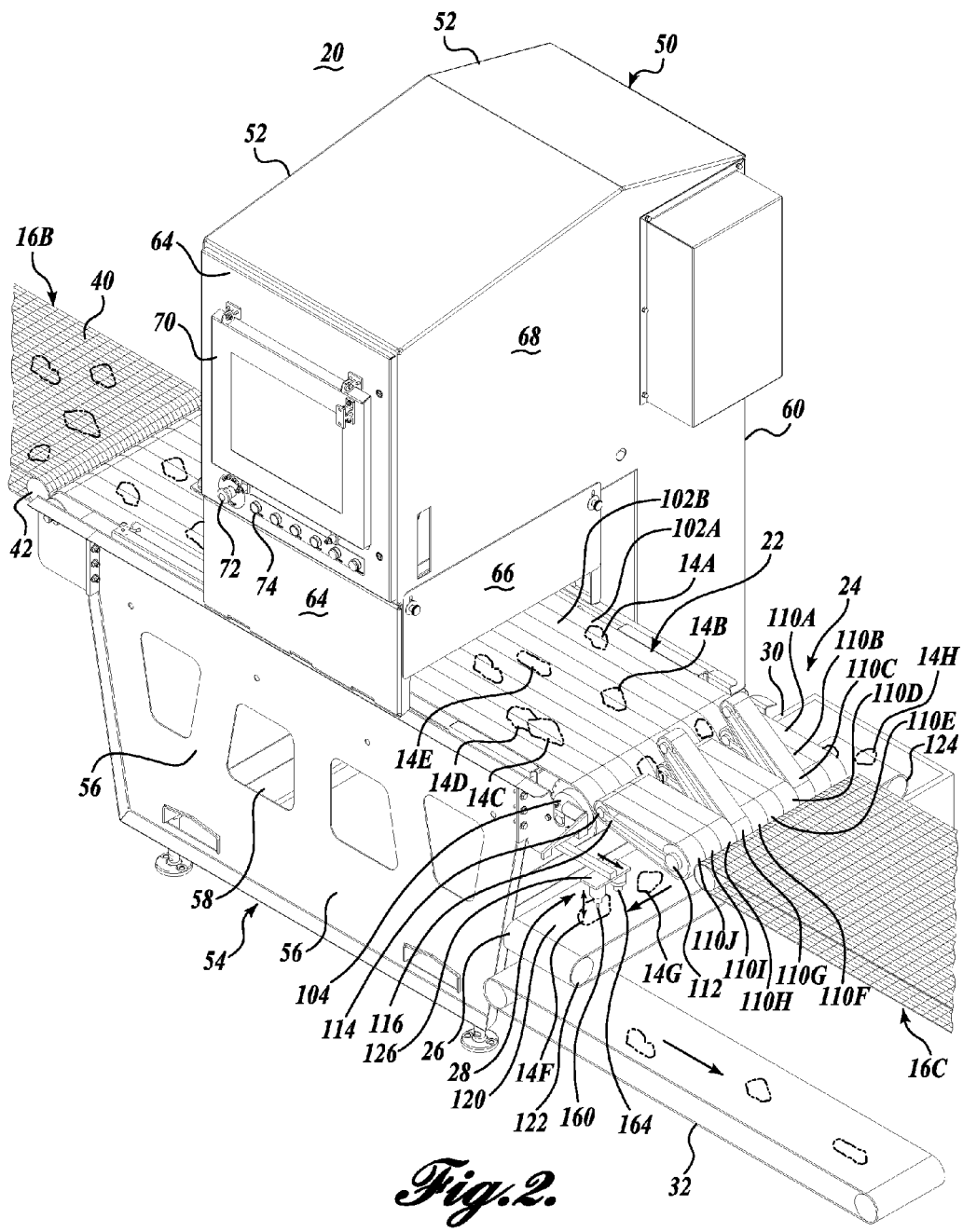
FIG. 2 is a pictorial view of a subsection of the thermal process control system of the present disclosure, with some components shown schematically.
Figure 3:
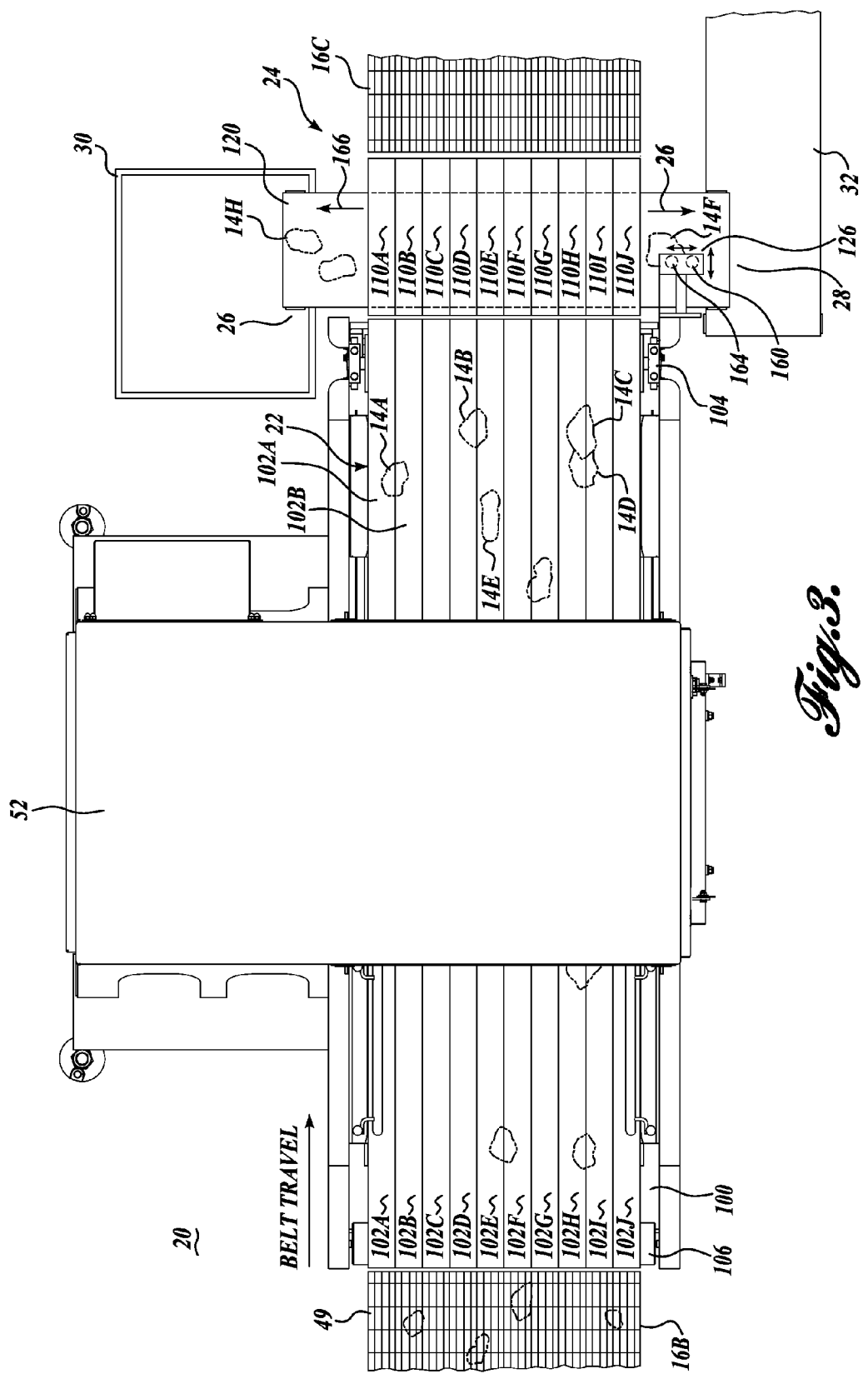
FIG. 3 is a top plan view of FIG. 2.

Describing the above basic components of system 10 in greater detail, the conveyor 16 may be of various standard constructions and powered in a standard manner. The conveyor 16 is illustrated in FIGS. 2 and 3 as utilizing an open mesh or link-type belt 40 that is trained around roller assemblies, including roller assembly 42, that may be powered or unpowered. An encoder, not shown, may be integrated into conveyor system 16, including sections 16A and 16B. The encoder may be configured to generate pulses at fixed distance intervals corresponding to the movement of the conveyor thereby to indicate the speed and displacement of the conveyor, which information can be used to keep track of the locations of food products 14 carried by the conveyor once identified at scanning stations 18 and/or 20.

Scanning stations 18 and 20 may have constructional and operational features that are very similar or the same and thus, the following description, unless otherwise indicated, applies to both scanning stations 18 and 20, though only scanning station 20 will be specifically referenced in detail. The scanning station 20 includes a scanning device 50 having a housing 52 positioned above conveyor section 22 and supported by an underlying frame 54. As shown in FIG. 2, the frame includes major side panels 56, extending lengthwise of conveyor section 22, and are transversely connected together by a plurality of cross-members 58. The cross-members 58 also tie into a housing base portion 60 that extends downwardly from housing upper portion 52 to the level of the floor 62 on which the scanning station 20 rests.

The housing upper section 52 includes a forward face panel 64 that extends downwardly to be supported by frame 54, see FIG. 2. Removable side skirt panels 66 depend downwardly from the side panels 68 of the upper housing section 52 to fairly closely overlie conveyor section 22. The side skirt panels 66 are used to contain the light utilized in conjunction with the operation of the scanning station 20. However, such panels are removable when requiring access to conveyor section 22, for instance, for cleaning or servicing.

A touch screen interface panel 70 is shown as mounted on housing forward face 64. Also various control knobs 72 and 74 are positioned beneath the touch screen panel 70 for use in operating the scanning station 20 and optionally for other purposes.

The scanning stations 18 and 20 may utilize a variety of different scanning technologies in the visible light as well as hyperspectral range. One visible light technology employs a video camera (not shown) to view workpieces, such as food products 14, along a line of sight which is schematically labeled as 80, see FIG. 4. The workpieces 14 are illuminated by one or more light sources, for example, by a laser beam, schematically depicted as part number 82 in FIG. 4. The laser beam 82 extends across the moving conveyor section 22 to define a sharp shadow or light stripe line, with the area forwardly of the transverse laser beam being dark. When no workpiece is being carried by the conveyor section 22, the shadow line/light stripe forms a straight line across the conveyor section. However, when a workpiece 14 passes across the shadow line/light stripe, the upper, irregular surface of the workpiece produces an irregular shadow line/light stripe as viewed by the camera, which is directed diagonally downwardly on the workpiece and the shadow line/light stripe. The camera depicts the displacement of the shadow line/light stripe from the position it would occupy if no workpiece were present on conveyor belt section 22. This displacement represents the thickness of the workpiece along the shadow line/light stripe. The length of the workpiece is determined by the distance of the belt travel of conveyor 22 that shadow lines/light stripes are created by the workpiece. In this regard, an encoder, not shown, is utilized in conjunction with conveyor 22, with the encoder generating pulses at fixed distance intervals corresponding to the forward movement of the conveyor 22.

In lieu of a video camera and light source, the scanning stations 18 and 20 may instead utilize an X-ray apparatus (not shown) for determining the physical characteristics of the workpieces 14, including their shape, mass, and weight. X-rays may be passed through the workpiece in the direction of an X-ray detector (not shown) located beneath conveyor 22. Such X-rays are attenuated by the workpieces 14 in proportion to the mass thereof. The X-ray detector is capable of measuring the intensity of the X-rays received thereby, after passing through the workpieces. This information is utilized to determine the overall shape and size of the workpieces, as well as a mass thereof. An example of such X-ray scanning device is disclosed in U.S. Pat. No. 5,585,603, incorporated by reference herein. The foregoing scanning systems are known in the art, and thus are not novel per se. However, the use of these scanning systems in conjunction with other aspects of the described embodiments are believed to be new.

Scanning in the hyperspectral range can be by reflectance spectroscopy techniques or by the use of other existing technology.

The data and information measured/gathered by the scanning stations 18 and 20 are transmitted to computing device 34, which is capable of recording the location of the work products 14 on the conveyor section 22 as well as the shape, thickness, size, outer perimeter, area, exterior condition or texture, and other physical parameters of the work products. The computing device 34 can be used to determine and record these physical parameters with respect to the work products as they exist on the conveyor section 22. As discussed below, the computing device 34 can also be used to record the temperature of the work products as measured downstream from scanning station 20 at temperature measuring station 28. In addition, the computing device, upon the information received from scanning system 18, can initiate various actions including, for example, altering the process conditions for the thermal processing station 12, notifying personnel of problems in the manner in which work products are being processed at station 12, or diverting work products from the processing station 12, for example, the work products that are outside of an acceptable range of one or more physical parameters, such as maximum thickness.

The computing device also can be used to record physical parameters of the work product 14 prior to processing at thermal processing station 12 and then subsequent to such processing, whether such processing involves cooking by steaming, frying, baking, roasting, grilling, boiling, etc. As discussed more fully below, optionally system 10 may utilize only one of the scanning stations 18 and 20. If only scanning station 18 is utilized, the information from scanning station 18 can be used to model the workpieces even after being thermally processed at station 12. Although typically shrinkage or change in shape of workpieces after thermal processing is not symmetrical and not easily quantifiable, such change is capable of being modeled with the use of a computing device. Such models and the data relative thereto may be stored in the memory portion 90 of the computing device. Such models and data can be employed to determine physical aspects of the workpieces after thermal processing and before measuring the temperature of the workpieces at thermal measurement station 28.

As shown in FIG. 1, the computing device 34 includes a central processing unit 92 as well as a memory 90. As noted above, the data concerning the workpieces, including their shapes, sizes, weights, and thicknesses, as well as the effect on the workpieces of further processing, may be stored in the computer memory 90. The information stored in memory can be easily selected by the user via interface 70 in the form of a touch screen panel or other interface device.

As also shown in FIG. 1, the computing device 34 may be in communication with a network system 94, which enables the computing device to communicate with and share information with other computers. The computing device 34 may also control and drive other equipment and hardware that is described below in addition to the scanning stations 18 and 20, the conveyor 16 and conveyor section 22.

As briefly noted above, the thermal processing station 12 may be used to process the workpieces in the form of food products in one or several manners. For example, one or more cooking processes may be utilized. For example, the food products may be cooked by steaming, frying, baking, roasting, grilling, boiling, etc. In this regard, the cooking processes may be carried out by convection, conduction, condensation, radiation, microwave heating, or by other techniques or systems. Also, different heating media may be utilized in the cooking process, including utilizing heated air or water, as well as steam.

In one typical thermal processing station configuration, the heating medium used for cooking, frying, baking, or roasting in an oven or frying in a fryer, or boiling, is supplied via a large, remotely located, natural gas-fired heat exchanger and corresponding storage tank for a thermal fluid. The heated thermal fluid is pumped through a further heat exchanger at the oven or fryer, etc., to provide heat to the oven or fryer, or boiler, etc. The thermal heating medium is then circulated back to the heat exchanger/storage tank, where the heating medium is reheated. Typically, heating devices of this nature are generally either fully off or fully on. In this regard, if workpieces, for example food products, have not entered the oven or fryer for a period of time, the demand for the heat at the oven, fryer, etc., drops and the gas-fired heat exchanger/tank shuts off. However, if relatively suddenly a large quantity of food products enter the oven or fryer, a length of time is required before it is sensed that the oven or fryer is cooling, and that the heating medium is not being heated. By the time the heating medium is sufficiently heated again, the oven or fryer may have cooled to the level that the food product passing therethrough may be under-processed. As part of the present disclosure, scanner 18, in conjunction with computing device 34, is capable of recognizing that operation of a thermal processing station may have slowed or even stopped, but suddenly needs to be restarted due to the arrival of food products to the thermal processing station. A signal is sent to the gas-fired heat exchanger/tank to immediately restart, and thereby minimize temperature swings in the food products processed at the thermal processing station. The present disclosure is capable of carrying out this "feed forward" control function. In this regard, the scanner 18 functions as a food product flow sensor.

The thermal processing via system 10 is not limited to cooking of the food products, but rather could involve the chilling, proofing, drying, or freezing of the food products. In this regard, the thermal processing station 12 may be a chiller, proofer, dryer, freezer or similar system and the thermal medium can be a chilled or low temperature fluid medium that is cooled by a refrigeration system.

As noted above, the workpieces in the form of food products 14 or other type of workpieces may be transported through the thermal processing station 12 by a conveyor system 16 or other transport system. It is common in industrial thermal processing stations for the station to have its own internal conveyor system to move the food products through the station while the food products are being thermally processed.

Various control parameters may be utilized in the operation of the thermal processing station 12. Such control parameters may include, but are not limited to, the speed at which the workpieces in the form of food products are transmitted through the station, as well as the volume or mass of the food products passing through the thermal processing station per unit of time. The control parameters may also include the humidity within the thermal processing station, as well as the temperature of the heat transfer medium, whether hot or cold air, hot or cold liquid, or other medium. If microwaves are utilized in the thermal processing station, the intensity level of the microwaves can be used as a control parameter.

As noted above, a conveyor section 22 is utilized in conjunction with scanning station 20. The conveyor section 22 includes a belt 100 that is of one piece construction or optionally can be divided into a plurality of separate lanes, for example, 102A through 102J. Such lanes may be created or indicated on belt 100 by vibratory laning posts, striping, indentations or ridges formed in the belt itself, or other means. The belt 100 trains around a downstream powered roller assembly 104 and an upstream idler roller assembly 106. Although not shown, one or more tensioning rollers may be utilized, for example, in conjunction with the lower return run of belt 100. An encoder, not shown, may be utilized in conjunction with belt 100 so that the scanning station 20 is capable of keeping track of the location of the various workpieces, for example, food products 14, identified and characterized by the scanning device 50 of the scanning station. In this regard, the scanner 50 can determine the physical parameters of the food products, including their size, shape, and thickness, as well as the location of the food products on the conveyor belt 100, and in particular, what lane or lanes in which a particular food product is located. The scanner is also capable of ascertaining whether food products may be overlapping each other, such as food products 14C and 14D, shown in FIG. 2.

A diverter conveyor section 24 is located in registry with the downstream end of conveyor 22. The purpose of the diverter section 24 is to divert selected food products 14 from conveyor 22 to a underlining transverse conveyor 26, on which food products are supported during temperature measurement thereof. The diverter conveyor 24 includes individual conveyor lanes 110A through 110J. Each of the conveyor lanes trains around a drive roller assembly 112 and an idler roller assembly 114 that are connected to opposite ends of a frame 116 extending between the drive roller assembly and idler roller assembly.

As shown in FIGS. 2 and 3, each of the conveyor lanes 110A through 110J are aligned with corresponding conveyor lanes 102A-102J of belt 100 of conveyor 22 associated with scanning station 20. In addition to being individually powered, each of the diverted conveyor lanes 110A-110J may be selectively pivoted individually or in pairs or groups about drive roller assembly 112, thereby pivoting upwardly the opposite upstream end of the conveyor lane(s) so that the food product being carried by the corresponding lane(s) of belt 100 falls off the belt 100 and onto the transverse conveyor 26 that underlies diverter conveyor 24. For food product 14A, only conveyor lane 110B needs to be pivoted upwardly to enable the food product to drop down to transverse conveyor 26. However, for food product 14B, conveyor lanes 110D and 110E must both be pivoted upwardly to enable food product 14B to drop down onto transverse conveyor 26. Once the selected food product has dropped downwardly from belt 110 to transverse conveyor 26, the applicable conveyor lane(s) 110A-110J may be returned to its normal operational position. If the food product in question is not to be diverted onto the transverse conveyor 26, the food product simply passes over the diverter conveyor 24 and onto the conveyor section 16C of the main conveyor 16.

The transverse conveyor 26, as noted above, is located below the diverter conveyor 24. The transverse conveyor includes a belt 120 trained about end rollers 122 and 124, one or both of which may be powered to drive the belt in either direction along the length of the conveyor, thereby to position the selected food pieces 14 at a temperature measuring station 28 adjacent one side of diverter conveyor 24, or a receptacle 30 located beneath the opposite end of the belt 120. One purpose of the transverse conveyor 26 is to position work products, such as food product 14F, in a proper location so that the temperature of the food product may be measured at the temperature measurement station 28.

The temperature measurement station 28 includes an extendible temperature probe 160 mounted on a single or multiple axis carriage system 162 located slightly laterally from the transfer conveyor 26. Carriage system 162 can be of various configurations, including an X-Y powered slide system. Rather than the carriage system, the thermal probes 160 may be mounted on a rotating arm structure wherein the probe is movable lengthwise of the arm, and the arm is rotatable about a vertical axis. A scanning device in the form of a camera 164 may be utilized in conjunction with a temperature probe 160 to help position the temperature probe relative to the food product in question. In this regard, the camera can be used to locate the centroid of the food product or the center of mass of the food product. The temperature probe 160 can be of various types of configurations. In one form, the temperature probe 160 can be of a thermocouple construction. The data from the temperature probe 160 can be transmitted to computing device 34, either by hardwire or by wireless transmission. This information can be processed to determine whether or not the food product has been sufficiently thermally treated, for example, if heated to a sufficiently high temperature to be cooked to a desired level, or cooled to a sufficiently low temperature. If the temperature processing of the food product has not been sufficient, the transverse conveyor can be powered in the direction of arrow 166 to deposit the food product into container 30 for re-processing. Rather than utilizing the container 30, a takeaway conveyor, not shown, can be substituted to transfer the identified food product for further processing or re-processing.

If, on the other hand, the food product has been adequately/properly thermally processed, the transverse conveyor 26 can be operated to deposit or transfer the food product in question to return conveyor 32, which then places the food product back into the main stream of processed food products moving along conveyor 16.

As noted above, temperature probe 160 is designed to extend downwardly into the food product to measure the temperature thereof. In this regard, the temperature probe may be mounted on a linear actuating device, which could take many forms, including, for example, a pneumatic or hydraulic cylinder, a roller screw actuated by a rotating nut, a piezoelectric actuator, etc. Such actuators are articles of commerce. Although a singular thermal probe 160 is shown in FIGS. 2-5, instead two or more probes may be used, thereby to measure the temperature at different locations in the food product. This can provide a more accurate measurement of the actual temperature of the food product.

Figure 4:
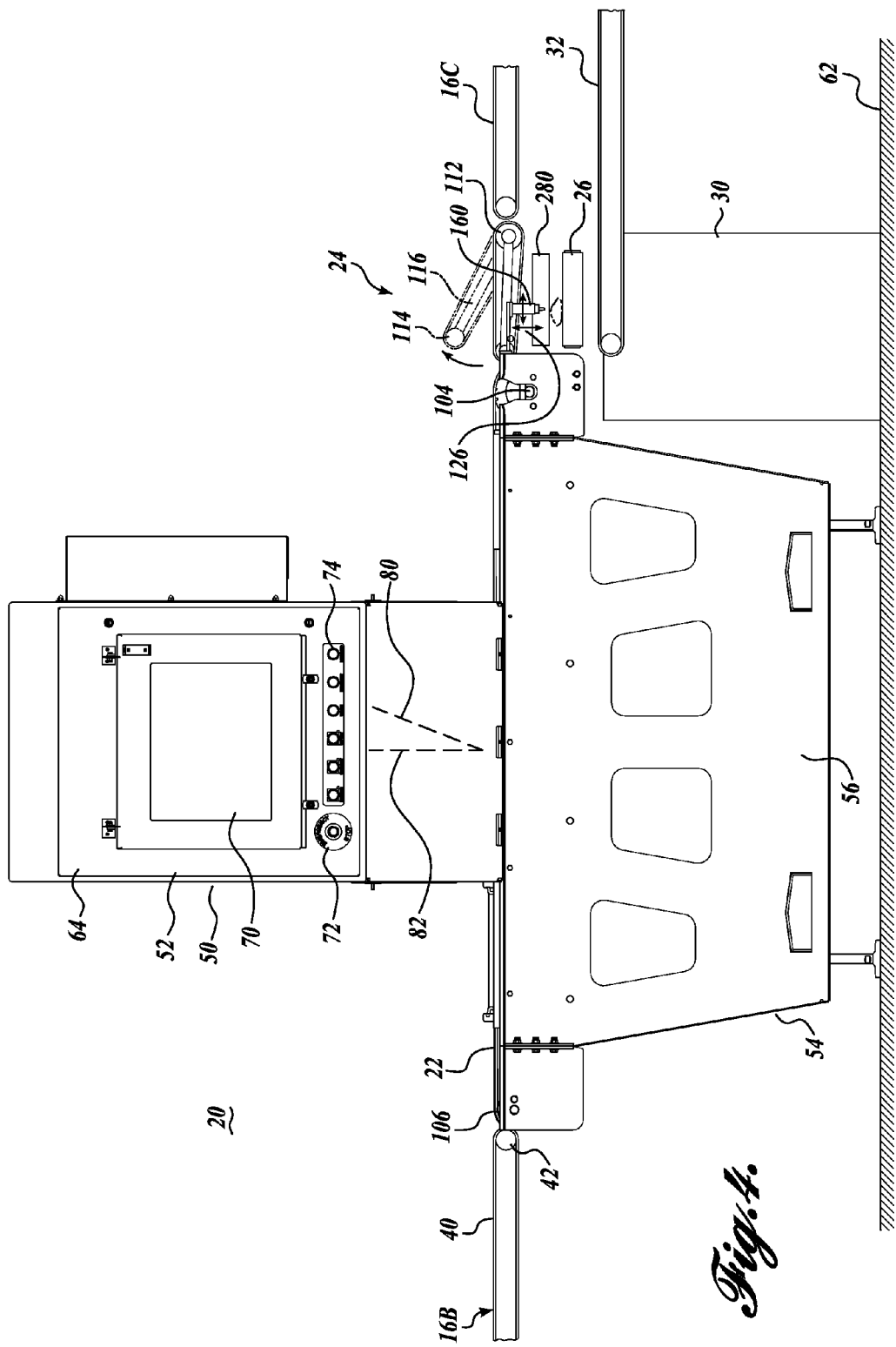
FIG. 4 is a side elevational view of FIG. 2.
Figure 5:
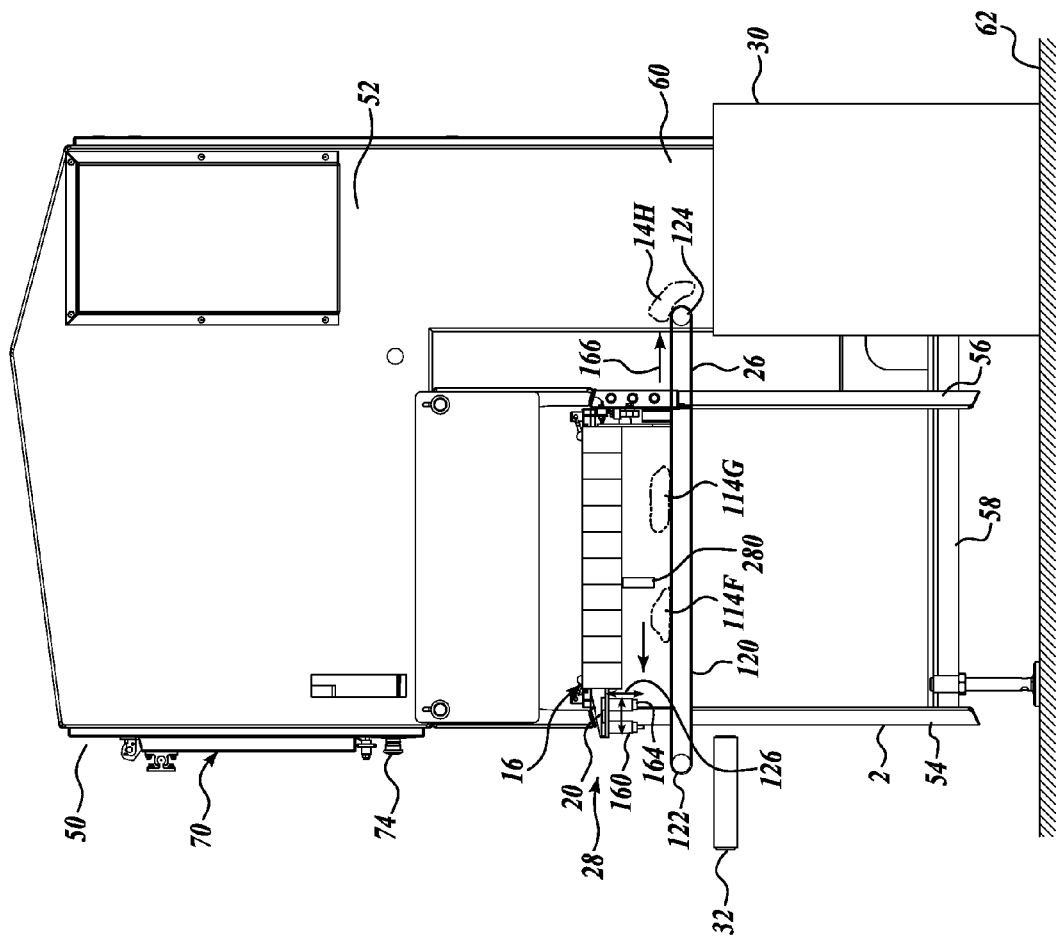
FIG. 5 is a front elevational view of FIG. 2.

As noted above, and as shown in FIGS. 2 and 3, it may be that workpieces, such as food products 14D and 14E, are at least partially overlapping each other on the scanning conveyor 22, or when dropped off the scanning conveyor, and then landing on the transverse conveyor 26. If the food products are in an overlapping condition on the transverse conveyor, there is a reduced likelihood of obtaining an accurate temperature measurement of the food product. To reduce this possibility, one or more abutment walls 280 extend transversely above and across transverse conveyor 26, as shown in FIG. 4. The lower edge of the abutment wall 280 is spaced above the upper surface of transverse conveyor belt 120 at an elevation higher than the thickness of a single food product, but not as high as the elevation of a second food product, if stacked on a lower food product. As a consequence, via the operation of the transverse conveyor 26, the abutment wall 280 will bear against the upper food product and separate the upper food product from the lower food product. It will be appreciated that one or more abutment walls of the nature of abutment wall 280 may be utilized along the length of the transverse conveyor 26.

Figure 6:
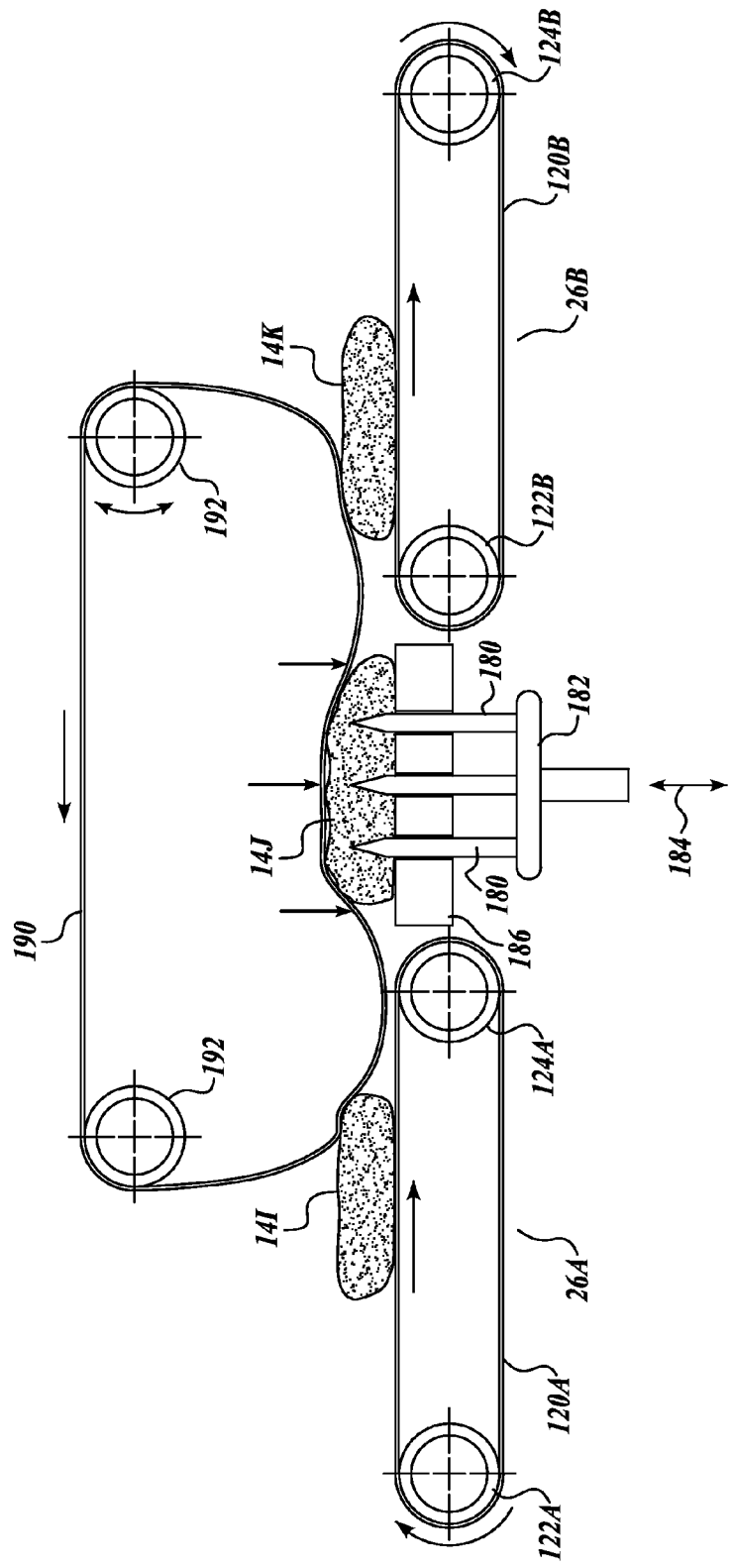
FIG. 6 is an enlarged, fragmentary view of another aspect of the present disclosure.

FIGS. 2-5 illustrate the thermal probe 160 extending downwardly into the workpiece in the form of food product 14, FIG. 6 shows a further embodiment for measuring the temperature of the food product, wherein three temperature probes 180 are illustrated as mounted on the base 182 for vertical movement in the direction of arrow 184. Temperature probes 180 extend through close fitting through holes formed in platform 186 on which food product 14J is positioned. The food product 14J is moved toward the platform 186 by transverse conveyor section 26A. Such conveyor section includes an endless belt 120A trained around end roller assemblies 122A and 124A. The transverse conveyor section 26A advances the food product 14 towards the platform 186, and when the food product approaches the platform, an overhead belt 190 that is draped over and overlies a portion of belt 120A engages the top surface of the food product 14 to urge the food product from the belt 120A and onto temperature measuring platform 186. One or more sensors determines that the food product has reached the proper measurement location, halts the conveyors 26A and 190 and initiates the upward movement of the probes 180. The overhead belt 190 is trained about upper roller assemblies 192, one or more of which can be powered to rotate in the desired direction. The belt is draped over the food product 14J and conforms to the contour of the top surface of the food product, but is capable of urging/moving the food product from belt 120A onto the platform 186. This enables the food product 14J to be placed in desired position while retaining the shape of the food product. Further details on this type of conveyance system are set forth in U.S. patent application Ser. No. 12/186,445, which is incorporated by reference into the present application.

While the food product is positioned on the platform 186, the overhead belt 190 is stationary and can apply a downward load on the food product to hold the food product in place while the temperature probes 180 are inserted upwardly into the food product. Once the temperature of the food product has been measured, the probes 180 are retracted downwardly so that they are withdrawn from the food product, thereby allowing the belt 190 to move the food product onto transverse belt section 120B for movement away from the temperature measuring platform 186. The belt section 26B, like belt section 26A, includes an endless belt 120B that is trained about end roller assemblies 122B and 124B. The transverse belt section 26B can direct the food product 14 to various locations including, for example, to a location for re-processing if need be, or to rejoin the other food products for further processing in the normal course.

As noted above, probes 180 are carried by a base 182 for vertical movement in the direction of arrow 184. The movement of the probes 180 is preferably in a prescribed manner, wherein the probes 180 are initially inserted quite quickly to a sensing position that is somewhat below the middle of the thickness of the food product 14J. Thereafter, the probes are moved upwardly more slowly to approximately the center of the thickness of the food product and then somewhat beyond the center of thickness of the food product. Thereafter, the probes are relatively quickly withdrawn downwardly. This prescribed motion of the probes 180 is based on the premise that the exact center of the thickness of the food product may not be accurately known, and there may be voids in the food product that can result in an erroneous reading. However, by taking many readings during the slower motion of the probes through the middle of the food product, the lowest temperature of the food product can be determined. This lowest temperature can then be analyzed regarding whether a thermal processing of the food product has properly occurred. Of course, if the food product is to be cooled or frozen, then through the prescribed motion of the temperature probes 180, the highest temperature of the food product can be found by the foregoing technique.

Periodically, the temperature probes 160 and 180 are cleaned or otherwise treated so that they remain in sanitary condition. This can be accomplished by numerous techniques, such as by induction or convection heating, heating by steam or hot air, heating by electromagnetic radiation, or heating by electrical current. The temperature probes may be sterilized after each use, or after a selected number of uses.

Figure 7:
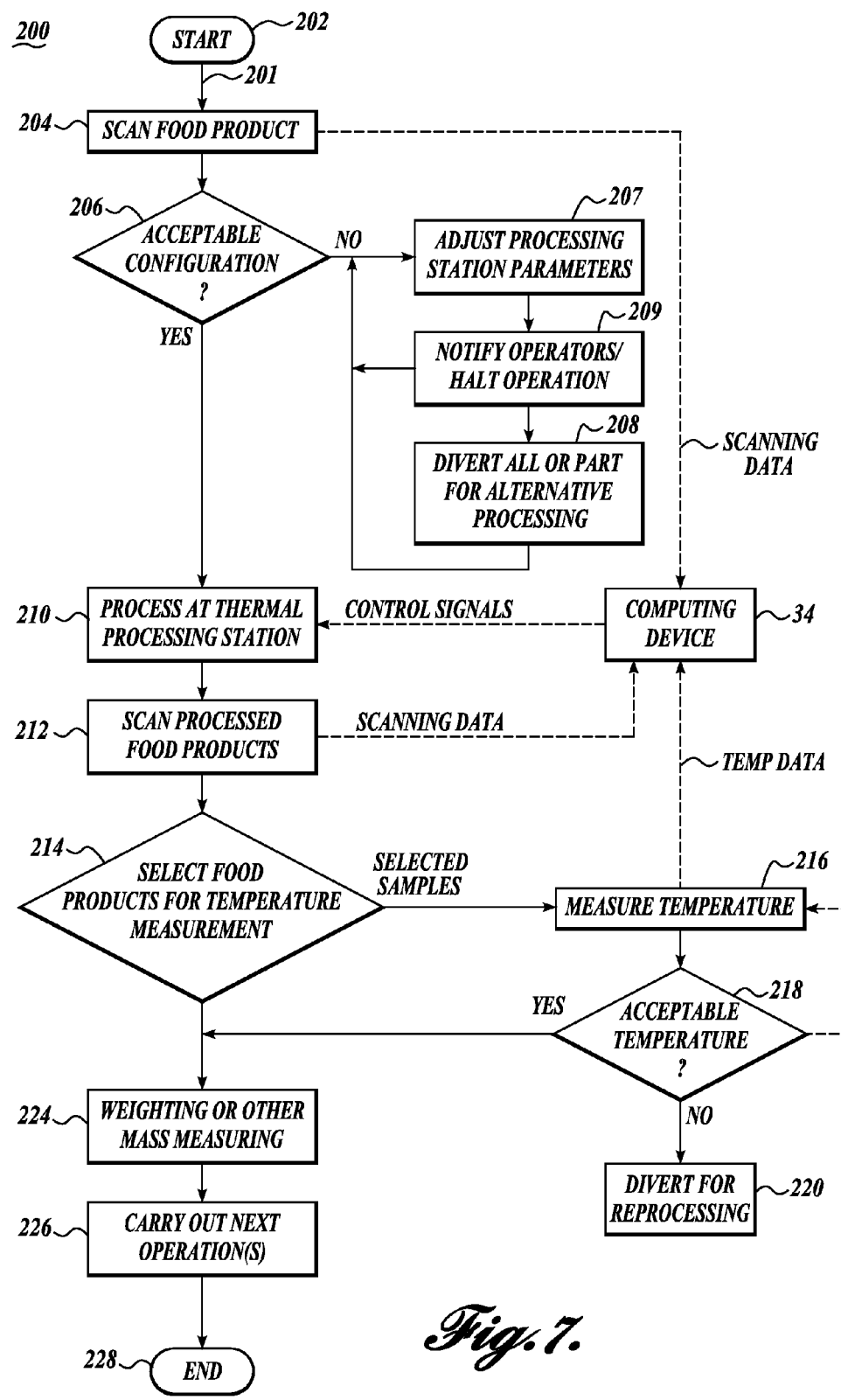
FIG. 7 is a flow diagram of one method of the present disclosure.

An overall method 200, in accordance with the present disclosure, is illustrated in the flow chart of FIG. 7. The method starts at 202 and includes step 204 of scanning workpieces, for example, food products traveling along a product stream 201 toward a thermal processing station, such as station 12 shown in FIG. 1. The food products are scanned, and the scanning data is used to determine physical attributes of the food products, including, for example, the volume, mass, thickness, centroid, area, texture, surface condition, and other physical features of the food products. In this regard, the scanning data is transmitted to computing device 34 for processing and analysis of the scanning data. Based on the data received from the scanning step 204 and the analysis of that data by computing device 34, various actions can be taken at step 206 that are initiated by output signals from the computing device 34. As a first possibility, at step 207 the computing device may send operational signals to the thermal processing station to alter process parameters at the thermal processing station, for example, as noted above, for a thermal processing station in the form of an oven or similar cooking apparatus or a freezer or cooler. Other parameters that may be changed in ovens or freezers include the volumetric flow rate of the thermal processing medium or fluid. For a thermal processing apparatus in the form of an electric fryer or heater, the level of electrical power to the fryer/heater can be altered. Further, for a thermal processing station in the form of an infrared or radio frequency oven, the power level to these units can be altered. The humidity in the thermal processing station and/or temperature of the heating/cooling medium used for thermal processing. Also, the processing time of the food product in the thermal processing station may also be altered. Signals may be also sent to other components of the control system 10 which have an effect on the processing of the food products, for example, the speed at which food products enter the thermal processing station.

In addition, as described above, the information from the scanning step 204 can be used as a feed forward control system to control the operation of the heating or cooling system used for thermal processing at processing station 12.

As an alternative to directly varying the process parameters of the thermal processing station or operational parameters at other locations of the process control system 10, the determination at step 206 may instead cause the computing device 34 at step 209 to send a notification to operational personnel that adjustments are required in the processing of the food products or that significant problems exist at the thermal processing station or elsewhere. Notification of operational personnel can be via different means, including email, telephone call or message, pager, horn, or other audio signal, flashing lights, etc. In addition to or as an alternative to sending notifications to operational personnel, the control system of the present disclosure could stop the processing of the food product, including shutting down the thermal processing station. Control specifications or limits can be set in advance so that a desired action(s) is/are taken depending on the extent of the deviation between the measured parameters or specifications from the scanning of the food products and the desired range or limits in parameters and specifications of the food products.

As a further option or possibility at step 206, a decision can be made whether food products should continue along the product stream to processing station 12 or be diverted for alternative processing at step 208. This decision is made based on the scanning data and the analysis thereof. It may be that the scanning results indicate that specific food products are either too large or too small, or too thick or too thin, etc., to be successfully processed at the thermal processing station 12. In that case, such food products that are not of acceptable configuration can be diverted to alternative processing at step 208. This diversion option is typically feasible when a majority of the workpieces are within a desired specification but there are occasional outliers, or perhaps if occasionally one food product is lying on top of another food product. By diverting the outliers, the remainder of the food products can continue on to be processed at station 12.

As a further possibility, rather than halting operation of the thermal processing system, it is possible to decide at step 206 to divert (at least for a limited time period) all of the out of parameter food products from the main flow stream 201 for alternative processing. Such diversion of the food products would require a diverting system which may be similar to diverter conveyor section 24 discussed above.

On the other hand, if the food products are of acceptable physical specification, the food products continue along the food product stream 201 to the thermal processing station 12 for the processing of the food product at step 210. Various control parameter algorithms can be utilized in conjunction with the processing that occurs at thermal processing step 210. Data for use by the control system algorithms is received from the computing device 34, which data can originate from the scanning data obtained from the scanning step 204. This process of transmitting control system information to the thermal processing station creates a closed loop system, whereby information about the food products traveling towards the thermal processing station can be factored in to the manner in which the thermal processing station is operated, including adjusting the thermal processing time of the food products and other process settings, such as the humidity within the processing station and the temperature within the processing station and/or the temperature of the heat transfer medium used to cook, cool, freeze, or otherwise process the food products at the thermal processing station. However, the power level to these processing stations, as well as to fryers, infrared ovens, radio frequency ovens and other thermal processing stations can be adjusted.

As noted above, one of the physical parameters of the workpieces that may be modeled from the scanning data is the thickness of the food products. It is known that industrial cooking processes are very sensitive to minor differences in product thicknesses. For example, a product that is 20 mm thick can take up to 23% more time to cook than a product that is 18 mm thick under the same cooking conditions. Thus, the thickness differential of 11% between food products can result in a cook time differential of 23%. Thus, for an industrial cooking process to run efficiently, the food pieces must be near the same thicknesses. If not, and if cooking occurs based on the thickest food product, then thinner food products will typically be overcooked. Correspondingly, if the cooking process does not take into consideration the thickest food products, then the thickest food products may not be properly or sufficiently cooked.

Also, the scanning process will be able to ascertain whether food pieces are arranged fully or partially on top of each other, which can cause a risk of undercooked food pieces. These overlapping food pieces may either be rearranged or may be diverted for reprocessing at step 208.

After being processed at thermal processing station 12, the food products may be scanned by scanner 20 at scanning step 212. The scanning data from the scanning step can be transmitted to the computing device 34, as shown in FIG. 7. By scanning all of the food products leaving the thermal processing stations, particular food products can be selected for temperature measurement based on desired criteria. Such criteria may include one or more of the following physical attributes of the thermally processed food products: thickness; width; length; aspect ratio; area; volume; weight; surface temperature; color; surface texture. The thermally processed food products are selected at step 214 for either temperature measurement or for continuing along the product stream. The selection of the food products for temperature measurement can be based on various criteria, such as one or more physical attributes of the food product, by sweeping across the food product stream, and selecting food products from such sweeping procedure, from random selection, or other criteria.

If the food products are selected for temperature measurement, such food products are diverted from the main product stream 201 to a temperature measurement station 28 wherein the temperature of the food products is measured at step 216. This information is transmitted to computing device 34 for analysis. This analysis may take into consideration the timespan between the food products being diverted from the main product stream 201 and when the temperature measurement actually takes place. The temperature measurement data collected may indicate that a change is needed in the control system(s) for the thermal processing station. For example, if the temperatures of the sampled food products are too low, one or more adjustments may be needed to the processing parameters at the thermal processing station. For example, the speed at which the food products pass through the thermal processing station may need to be lowered, or the temperature of the heat exchange medium used in the thermal processing station 12 may need to be increased, or other control system adjustment made. On the other hand, if the temperature of the selected samples of processed food products is too high, then appropriate adjustments can be made to one or more of the process parameters via the control system algorithms utilized in conjunction with the thermal processing station.

As noted above, it is current industry practice to adjust the cooking process so that the center of the thickest food pieces reach a food safe temperature. However, this approach can cause a significant amount of the food pieces to be overcooked, which not only decreases yield, but also profit, since overcooking dries out moisture, resulting in reduced product weight and quality. Applicant estimates that overcooking on a single food processing line can have an annual negative economic value of hundreds of thousands of dollars. Moreover, if undercooking of food products can be avoided, then unscheduled line stoppage for cleaning and otherwise sanitizing the food processing line can be avoided, thereby increasing the amount of time the food processing line is operational. In addition, there is a lower risk of product contamination and lower potential for product recall. There is a significant direct savings as well as retention of brand value associated with avoiding a product contamination event.

Step 218 depicts the decision of whether, based on the measured temperature of the sampled food product, the food product is likely to have been acceptably thermally processed. If not, the food product can be diverted at step 220 for further processing. Also, other and/or additional remedial steps can be taken, for example, to temporarily stop or slow the conveyor to increase the dwell time of the food products in the thermal processor. However, if the temperature measurement indicates that the food product has been properly processed, then the food product can proceed to further processing, including by rejoining the food product stream 201.

In addition to determining whether the food products have been acceptably thermally processed in the manner of course of the operation of system 10, the present process can also be used to monitor whether changes in the food product detected at step 201 have caused a problem in the processing step of 210. For example, if the food products were detected by the scanning step 204 as being suddenly thicker or thinner, or larger or smaller, then such changes in the physical attributes of the food products may have resulted in the adjustment of processing parameters at step 207 to the processing of food products occurring at step 210. By measuring the temperature of the food product at step 216, it is possible to determine whether or not the adjustments made at step 207 were successful or not. This can be determined by measuring the temperature of the food product after one residence time within the food processing station.

The foregoing adjustment to the processing parameters at step 207 may have been for reasons other than detecting a change in the population of the work pieces, but rather, due to other changes in the thermal processing system, for example, a desire to increase the throughput of the system, and thus needing to shorten the thermal processing time at step 210. In this regard, operational parameters of the thermal processing station may have been adjusted, and the results of such adjustment can be monitored by monitoring the temperature of the food products exiting the thermal processing station after one residence time in the thermal processing station.

Another aspect of using a scanner for scanning all of the food products at step 212 that leave the processing station is that based on the temperature measurement data, it is possible to identify other processed food products that likely are unacceptable, and thus such food products can be diverted from the main food product stream 201 using the diversion equipment and procedures discussed above. In a typical operational mode, the temperature of about one food product per minute is measured. If such measured sample food product is found to be unacceptable, such food product can be diverted for further processing. Unless all of the food products from the thermal processing station are scanned, other similar unacceptable food products will continue along the food product stream 201. However, if all of the food products are scanned, food products having attributes similar to the unacceptable food product can also be automatically diverted from the main product stream.

Another benefit of scanning all of the food products leaving the thermal processing station 12 is that it is possible to perform a thermal processing station diagnosis and performance validation. In the thermal process diagnosis mode, food products of substantially equal thicknesses, across the width of the product stream, can be selected for temperature measurement. This enables a determination to be made if the thermal processing unit is processing uniformly across the full width of the product stream. For example, if a 40 inch wide oven includes a conveyor for carrying the food products through the oven having ten lanes each four inches in width, it is possible to select, for example, only 18 mm thick food pieces that appear in each lane as they occur. The temperature of such selected food products can be measured and color or other attributes of the food products can also be determined by the scanning step 212. If the heat is too cool at the sides or edges, or if air entrainment in the equipment is affecting color development in one region or side of the food product stream, these problems can be identified as well as in which of the product lane(s) the problems are occurring. Corrective measures can be taken to rectify the situation.

In process 200, the weight or mass of the processed food products is optionally weighed at step 224. Such weighing can occur by various means, such as by use of a platform scale, a tote scale, or other mass measurement system. This information can be combined with the total food product input rate at the beginning of the process 200 to determine the yield of the process on an hourly basis, a batch basis, a shift basis, etc. This information can be utilized to adjust the process 200, including adjusting the process parameters at the thermal processing station 12. Also, this information may indicate that the assumed density of the food product being utilized in the scanning step 204 may have to be adjusted if the data from the weighing step 224 shows a deviation from the expected weight of the food products based on the starting weight of the food products and the level of diversion of the food products occurring during process 200. After the weighing step 200, the food products continue on to subsequent operations at step 226, thereby reaching the end of the process 228.

Figure 8:
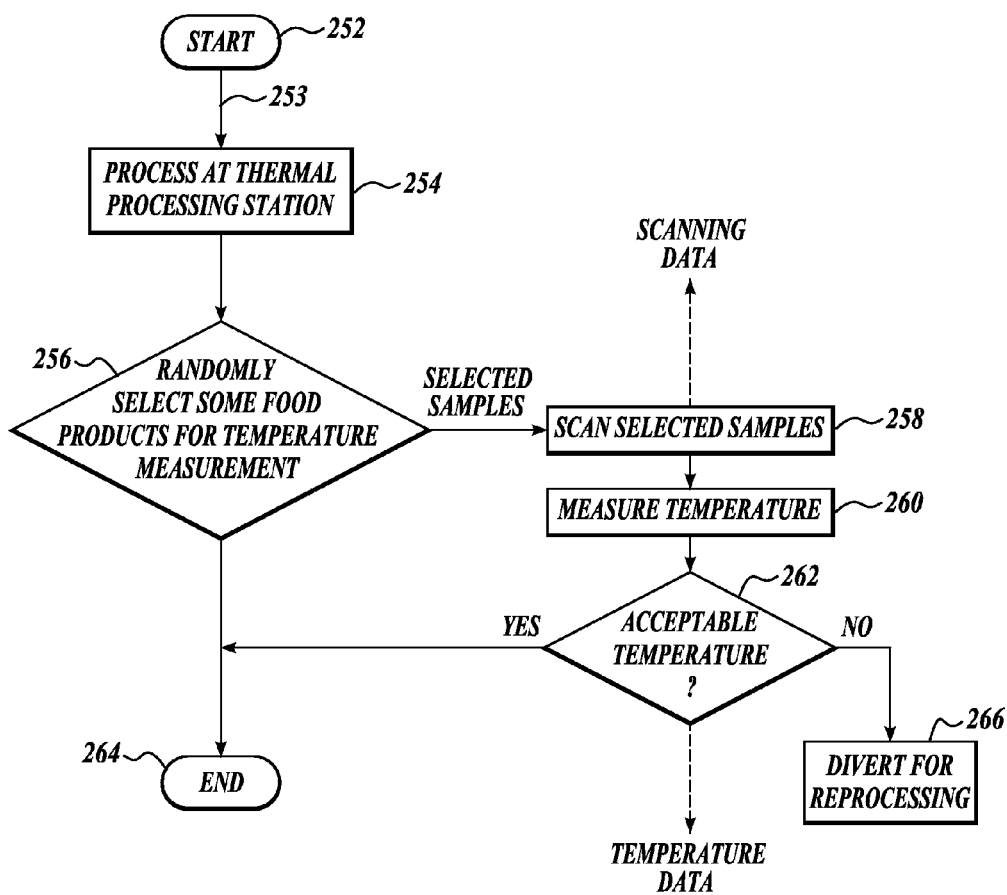
FIG. 8 is a flow diagram of a second method of the present disclosure.

FIG. 8 illustrates a further process of the present disclosure, wherein the process 250 may be employed as a "stand alone" process to be used in conjunction with existing food processing lines or equipment. Process 250 begins at the start step 252, wherein a stream 253 of food products are transmitted to a processing station and processed at step 254. After processing, the food products are randomly or otherwise selected for temperature measurement at step 256. Such selected food products are then scanned at step 258 to model desired physical attributes of the selected food products. Modeling also enables the location of the center of mass or centroid of the food product to be located so that in the temperature measurement step 260, a temperature probe or other device may be accurately positioned at the food product centroid or geometric center. At step 262, if the temperature measurement determines that the food product sample has been satisfactorily processed, then the food product in question may be returned to the main food product stream 253, and then the process concluded at step 264. However, if the temperature of measurement indicates that the food product in question has not been properly processed, then such food product can be diverted at step 266 for further processing. The data from the scanning step 258 and/or from the temperature measurement step 262 can be transmitted to a computing device for storage and also for use in analyzing the thermal process being carried out, as well as the operation 254 of the thermal processing station.

Further, if the temperature measurement step at 260 indicates that the food product has been underprocessed, then the temperature measuring instrument may need to be sanitized, so as not to cross-contaminate subsequent food products of which the temperature is measured. Even if the temperature measurements indicate that the food products have been properly and sufficiently processed, good practice indicates that the instrumentation used to physically determine the temperature of the food products, especially if a probe or other device is inserted into the food product, sanitation thereof should occur on a periodic basis. As noted above, this can take place by various means, such as by subjecting the temperature probe or other equipment to steam, placing the temperature probe or other equipment in boiling water, or in a stream of very hot air, etc.

In process 250, first and second scanning stations 18 and 20 are not utilized. Rather, limited scanning of selected food product samples occurs primarily to model the selected food product so that the temperature probe or other temperature measuring device can be properly located with respect to the selected food product. Such scanning can occur via one or more camera devices, such as camera 164, described above. Or other well-known scanning systems can be utilized instead. Due to the limited purpose and function of such scanning, the scanning device can operate quite quickly so as to not be a significant limitation in the temperature measuring process.

Use of camera 164 or other similar scanner can result in a much more accurate temperature measurement of the food product than if operating personnel must visually select what location in a food product in which to insert a temperature probe or other measurement device, and then actually inserting the probe or device in the food product. As noted above, there are at least two sources of error in such manual operation. A first source of error occurs when determining where the optimum location exists in which to take the temperature measurement. A second source of error occurs in the actual placement of the thermal probe or other device into the food product. Nonetheless, it is contemplated that the system and methods of the present disclosure can be utilized in conjunction with manual temperature measurement of the food product. Even manual temperature measurement will provide advantages over existing techniques and methods for measuring the temperature of thermally processed food products.

It will be appreciated that through the present disclosure, it is possible to model the overall system 10 to evaluate multiple alternative values of control parameters if the results of the model indicate an issue is occurring in the thermal processing of food products or other types of workpieces. The modeling of the system can consider at least the following dynamics: (1) how changes in the flow rate of the stream of food products entering the processing station causes changes to the temperature in the processing station and/or the temperature of the heat transfer fluid (whether air, steam, or oil) used in the processing station; (2) how changes in the volume, thickness, or other geometric or physical parameters of the food product stream, particularly of the largest pieces of food products, cause changes in the heating rate of the individual food pieces in the thermal processing station; (3) how changes in the temperature of the stream of food products is related to other changes in the system or changes in the incoming food products, such as the speed of the transfer conveyor or the mass of the food products entering the processing station over time, and then updating the model of the overall system based on such measured results. As noted above, if the results of the system model indicate that the future temperature of the food products exiting the thermal processing station will be too high or too low, adjustments can be made to the processing parameters of the thermal processing station.

The modeling referred to in the previous paragraph predicts the temperature profile of the food products, especially when being thermally processed within the processing station 12. The modeled temperature profile of the food product can then be used to determine if the food product has been sufficiently/properly thermally processed. The methodologies that may be utilized in this regard can consist of a determination of whether or not the modeling indicates that the temperature within the food product has reached a minimum predetermined temperature sufficient to instantaneously kill the pathogens in question. As an alternative, modeling can be used to determine whether the level of pathogens within the food product has been reduced to levels required by government regulations. The modeling of the temperature profile of the food product can take into consideration various factors that are specific to the food product and also factors that are specific to the configuration of the processing system 10. Some of the factors specific to the food product include the type of food product, the density of the food product, the thickness range of the food product, the initial temperature of the food product, the latent heat of the food product, the fat content of the food product, the moisture content of the food product, and the loading level of the food product on the conveyor 16. Factors pertaining to the thermal processing system 10 may include, for example, the speed of the conveyor 16 and/or the dwell time of the food product within the processing station, the temperature within the processing station, including any variation of such temperature at different locations within the processing station, the moisture level of the heating medium utilized within the processing station and/or the rate and volume of the air circulation within the processing station.

It will be appreciated that such modeling of the system 10 can be used to confirm the accuracy of the measured temperature of the food products utilizing the system 10. Moreover, if the results of the modeling of the system 10 coincide with the results of the temperature measurements being taken of the food products 14, then it may be that the frequency at which the temperature of the food products is measured may be altered (reduced). On the other hand, if there is a significant deviation between the modeled temperature of the food products and the measured temperature of the food products, then it may be that the frequency that the temperature of the food products is measured may be increased.

Also, rather than taking into consideration all of the foregoing factors in the modeling of system 10, selected modeling parameters may be employed so that the modeling algorithms may be simplified and require less data processing than if a larger number of factors were utilized. Such selected modeling parameters might include the dwell time of the food products in the thermal processor and the temperature within the thermal processor.

It will also be appreciated that in the foregoing system 10 and method 200, the removal of selected sample food products from the product stream for temperature measurement enables the internal temperature of the selected food products to be stabilized. Typically, as food products are being heated, the internal temperature of the food product is at a lower temperature than the surface or near surface temperature of the food product. It takes a finite amount of time for the internal temperature of the food product to stabilize or rise towards the surface temperature of the food product. By removing the food product 14 from the food stream to measure the temperature of the food product, sufficient time is provided for the internal temperature of the food product to stabilize. Moreover, by removing the sample food products from the product stream for temperature measurement, the temperature of the food product can be measured utilizing standard temperature measurement devices which require several seconds to achieve an accurate temperature measurement of the sample food product. High-speed temperature measurement devices are available, but at a higher cost than more standard temperature measurement devices. Also, high-speed temperature measurement devices are typically of smaller size than more robust slower speed units. The smaller size devices are not as durable as larger, standard speed units.

Further, through the present system 10, the probe of a temperature measurement device can be inserted into the sample food product using automated equipment rather than relying on the ability or skills of a workman to manually determine where to insert a temperature measurement probe and then actually inserting the temperature measurement probe at the desired location or locations on the food product.

While illustrative embodiments have been illustrated and described, it will be appreciated that various changes can be made therein without departing from the spirit and scope of the invention.

As one change to the present disclosure, the thermal processing control system 10 may be configured with second scanning station 20, but not first scanning station 18. In this situation, changes, adjustments, or corrections to the processing parameters used at the processing station will rely upon the information and data from the scanning station 20 as well as from the temperature measuring station 28. Such data can be employed by the control system algorithms used in controlling the operation of the thermal processing station. In other respects, in this modified configuration, the advantages are provided as are achieved via the thermal processing control system 10 and the thermal processing method 200, described above.

As an alternative configuration, the thermal processing control system 10 may be configured with first scanning station 18, but not with the second scanning station 20. In this situation, all of the food products entering the thermal processing station are scanned, and the scanning data is transmitted to computing device 34 for processing and analysis of the scanning data. As also noted above, by scanning all such food products, it is possible to divert from the main food product flow stream those specific food products that are not likely to be successfully processed at the thermal processing station, for various reasons; for instance, if the food products are too small or too large, or too thick or too thin.

In addition, it is possible for the food products that are scanned at scanner 18, and then thermally processed, to be modeled as to the physical attributes of the food product after being thermally processed, whether the thermal process involves cooking, and whether such cooking is by steaming, frying, baking, roasting, grilling, boiling, etc. Typically, the shrinkage that occurs from thermal processing of food products is non-symmetrical and not easily quantifiable, but is capable of being modeled, especially with the use of a computing device. Such model(s) and data relative thereto may be stored in the memory portion 90 of computing device 34. Such model(s) and data can be employed to determine physical attributes of the food products after thermal processing. This enables the ability to select specific food products for temperature measurement after being thermally processed. Use of scanning information from scanner 18 in this manner may not be as accurate as employing a second scanner 20, but may be an acceptable alternative to requiring a second scanner 20, thereby to provide the benefits of the present disclosure without requiring the second scanner 20.

As another possible change to the present disclosure, a particular configuration of an apparatus for diverting food products from the food product stream was described above through the use of a conveyor diverter section 24. However, other means and systems can be utilized for diverting food products from the main food product stream, either for temperature measurement or for alternative processing, or for other purposes. Such diversion can occur by use of gravity, openings between conveyors, or using compressed air jets to blow desired food products off of the conveyor along which the food products are being carried.

The foregoing disclosure has described the use of the transverse conveyor 26 for directing workpieces, such as food products, to a thermal processing station. Of course, other configurations of conveyors can be utilized. For example, such conveyor could be located above, below, or parallel to conveyor system 16.

Although the foregoing disclosure describes the use of diverter conveyor section 24 and transverse conveyor 26 for transporting selected workpieces, including food products, to a temperature measuring station, this function can be carried out using a robot system, which can be in the form of an X-Y actuating system that is capable of dropping down to conveyor 16 and picking up the workpiece, then carrying the workpiece to another location or another conveyor. One such system is disclosed by U.S. Pat. No. 6,826,989, which is incorporated by reference into the present application. Also, U.S. Pat. No. 7,007,807 discloses the sorting of work pieces utilizing the "pick and place" system and structure of U.S. Pat. No. 6,826,989. U.S. Pat. No. 7,007,807 is also incorporated by reference into this present application.

Figure 9:
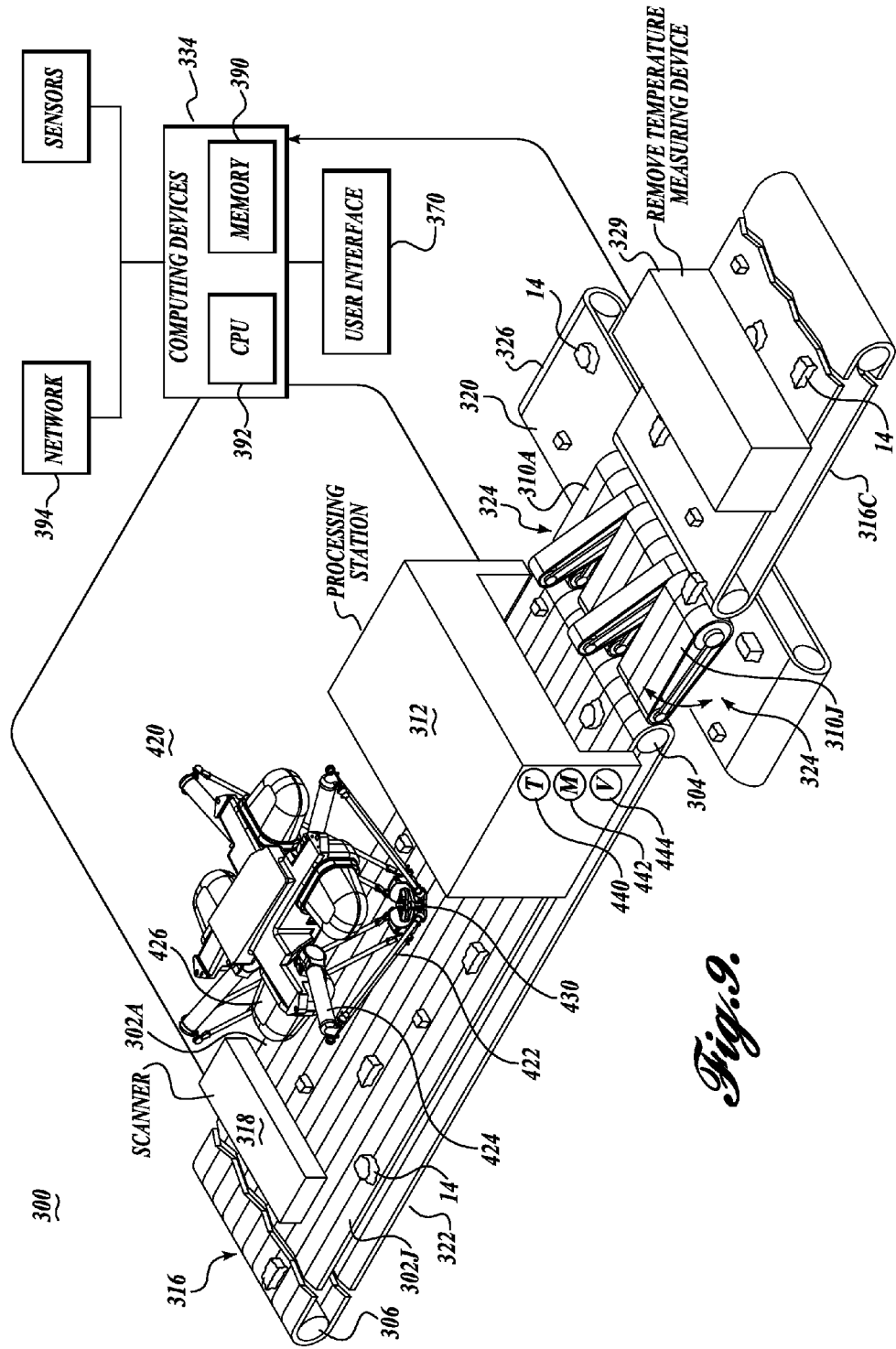
FIG. 9 is a schematic view of a further thermal measurement and process control system of the present disclosure.

Referring to FIG. 9, a thermal measuring, processing, and control system 300 in accordance with the present disclosure is illustrated. The system 300 has certain components or aspects that are the same or similar as system 100. In this regard, the comparable components or aspects of the system 300 that are similar or same to the system 100 are identified by the same part number but within the "300" series. Also, the comparable components will not necessarily be described in detail so as to eliminate duplication.

The system 300 includes a thermal processing station 312 for the processing of food products 14 that travel through the food processing station via a conveyor system 316. Upstream of the thermal processing station 312, the conveyor 316 carries food products 14 past a scanning station 318 for the scanning of the food products being carried by the conveyor section 316. Downstream of the thermal processing station 312, a diverter conveyor section 324 is capable of diverting food products 14 to an underlying transverse conveyor 326. The transverse conveyor 326 can transport the diverted food products for further processing or other remedial action. A temperature measuring device removal station 329 is located downstream of the diverter conveyor section 324 whereat, as described below, temperature measuring devices 402 are removed from the food products being conveyed by conveyor section 316C.

As in system 10, system 300 also includes a computing device 334 capable of receiving scanning information from scanning station 318 as well as temperature information from temperature measurement devices 402, described below and shown in FIG. 12. The information from scanner 318 as well as from the temperature measurement devices 402 may be utilized to determine whether the food products have been properly thermally processed. Such information optionally can be utilized to adjust and/or control the operation of the thermal processing station 312.

Describing the above basic components of system 300 in greater detail, a conveyor section 322 is utilized in conjunction with scanning station 318 and thermal processing station 312. The conveyor section 322 includes a belt 300 that may be of one-piece construction or optionally divided into a plurality of separate lanes, for example, lanes 302A-302J. Such lanes may be created or indicated on the belt 300 by vibratory laning posts, striping, indentations, ridges formed in the belt itself, or by other means. The belt 300 trains around a downstream powered roller assembly 304 and upstream idler roller assembly 306. An encoder, not shown, may be utilized in conjunction with the belt 300 to keep track of the location of the various work pieces 14 identified and characterized by the scanning station 318. Scanning at the scanner station 318 can determine the physical parameters/characteristics of the food products, including their size, shape, thickness, contours, area, composition, as well as the locations of the food products on the belt 300, and in particular, what lane or lanes in which a particular food product is located. The scanner 318 is also capable of ascertaining whether food products may be overlapping each other.

As in system 10 described above, the diverter conveyor section 324 is located in registry with the downstream end of conveyor section 322. The construction and operation of the diverter conveyor section 324 is described above. Also, the construction and operation of transverse conveyor 326 is described above.

Scanning station 318 may be of a construction and operation similar to scanning station 18 described above. In this regard, various different scanning technologies may be utilized in conjunction with the scanning station 318, as described above. The data and information measured/gathered by scanning station 318 is transmitted to computing device 334, which is capable of recording the location of the food products 14 on the conveyor section 322, as well as the shape, thickness, size, outer perimeter, area, exterior condition or texture, and other physical parameters or aspects of the work products. The computing device 334 can be used to determine and record these physical parameters with respect to the work products as they exist on the conveyor section 322. The computing device 334 also can be used to determine the temperature history or profile of the food product as it is processed in the processing station 312, and from such temperature or profile, determine whether adequate and complete thermal processing of the work product has occurred. Further, the computing device, upon information received from scanning system 318 and the measured temperature of the work products optionally can initiate various actions, including, for example, altering the process conditions for the thermal processing station 312, notifying personnel of problems in a manner in which work products are being processed at processing station 312, initiating remedial action on the work products if thermal processing of the work products has not been satisfactorily achieved, as well as taking other remedial actions to ensure that the system 300 remains in sanitized condition.

One distinguishing aspect of the system 300 is the utilization of thermal measurement devices 302 which are connected to selected sample work products at selected locations on the sample work products. The scanning station 318 scans the work products 14 on the conveyor 316 and from this information, particular work products can be identified as samples for temperature measurement. For example, such work products may be selected based on being of a specific thickness, including being of a thickness greater than the norm, or perhaps being of a specific size or area. Moreover, the scanning station 318 can provide specific information pertaining to selected sample work products, including the location on the sample work product that is the thickest, at which location the thermal measuring device may be attached or inserted.

Referring specifically to FIGS. 12 and 14, the thermal measuring device 402 may be constructed with a housing 404 and a probe 406 projecting from the housing. The temperature measuring devices 402 are designed for the probe 406 to be inserted into the sample food product at a desired location and depth and then the device travels with the sample food product through the thermal processing station so that the temperature of the sample food product can be measured and monitored and optionally recorded during the thermal processing of the sample food product. Temperature sensor elements for the temperature measuring devices 402 are located within the housing 404. The temperature sensor data can be transmitted from the devices 402 to the computing device 334 via wireless technology. Temperature measuring devices of the nature of devices 402 are articles of commerce.

The temperature measurement devices 402 can be inserted into the selected sample food products by an automated actuator system. One such actuator system 420 is illustrated in FIG. 9. The actuator system 420 is composed of four sets of powered arm pairs 422 that are each connected at one end (upper) to a powered pivot arm 424 which in turn is connected to a rotary actuator 426. The lower or opposite ends of the arm pairs 422 are connected to carrier head 430 which is capable of grasping temperature measurement devices 402, typically via the housing portion 404, with the probe portion 306 pointing downwardly.

The actuator system 420 is capable of moving the carrier head 430 in any direction over the conveyor section 322 as well as downward and upward relative to the conveyor section. The actuator system 420 may also tip or tilt the carrier head to a desired orientation. As can be appreciated, the actuator system 420 can place the temperature measurement devices 402 at selected locations on/in the food products that have been preselected via the scanning of the sample food product. For example, such location may be at the thickest location on the sample food product. The temperature measurement devices 402 may be held by the carrier head 430 by any appropriate means, for example, by articulating fingers, electromagnet, etc., not shown. Once the temperature measurement devices 402 have been inserted into the selected sample food products, the temperature measurement devices travel along with the sample food products through the thermal processing station 312.

As described above, the thermal processing station 312 may be of numerous types utilized to thermally process the food products. Temperature and moisture sensors 440 and 442 may be utilized to measure the temperature and moisture within the thermal processing station 312. Also, if the air within the thermal processing station is circulated, for example, using a fan system, an air velocity sensor 446 can also be utilized to measure the speed and volume of air flow within the thermal processing station.

As shown in FIG. 9, the temperature measurement devices 402 are removed from the sample food products 14 at removal station 329. The removal of the temperature sensing devices 402 can be accomplished by numerous different means. For instance, a magnet can be positioned above the temperature measurement devices 402 to draw the devices upwardly and out of the sample food products 14. Alternatively, an actuator, perhaps similar to actuator 420, can be utilized to remove the temperature measurement devices from the sample food products. As another possibility, the temperature measurement devices may be manually removed from the sample food products. As still another option, the temperature measurement devices may continue on with the sample food products as the food products are being further processed, and removed at a later stage of processing. This would enable the temperature of the sample food products to continue to be monitored during further processing.

An alternative configuration of an actuator 450 is illustrated in FIG. 12. As shown in FIG. 12, actuator 450 in basic form includes a support structure 452 extending across the conveyor 316 for supporting and guiding a carriage 454 having wheels 455 for rolling movement along the support structure in a direction transversely to the direction of movement of the conveyor. The carriage 454 is powered by a drive system including, in part, the motive system 456 that powers a drive belt 458 connected to the carriage 454. The belt 458 is powered by drive pulley 460. The belt also trains around an idler pulley 462. A second, longitudinal support structure or beam 464 is cantilevered outwardly from, and carried by, carriage 454 in a direction generally aligned with the direction of movement of the conveyor 316. A second, "longitudinal" carriage 466 is adapted to roll on wheels 467 along the beam 464 by a drive system which in part includes a second motive system 468 to power the longitudinal carriage 466 through a second drive belt 470 connected to carriage 466. An elongated track 472 is mounted on and extends longitudinally on the sidewall of beam 464 to guide wheels 467. The longitudinal carriage 466 is adapted to travel along track 472. The carriage 466 is moved back and forth along track 472 by the second motive system 468, constructed similarly to motive system 456, to power the drive belt 470 connected to carriage 466. The second belt 470 is driven by drive pulley 476. The belt 470 also trains around an idler pulley 478 located across the conveyor 316 from the drive pulley 476. The belt 470 further trains around an idler pulley 480 located at the distal end of beam 464.

A work tool 482, which may be in the form of a linear actuator, is mounted on and is carried by the carriage 466. The work tool 482 is movable relative to section 322 of conveyor 316 to pick up temperature measuring devices 402, position the temperature measurement devices at predetermined locations over selected sample work products, and then insert the temperature measurement devices downwardly into the sample work products. As can be appreciated, the work tool 482 is capable of moving along and across the conveyor 316 as needed.

It can be appreciated that rather than using beam 464 and second carriage 466, the work tool 482 can instead be mounted on the carriage 454 for movement across the conveyor 316.

Although not specifically illustrated, it can be appreciated that other forms of powered actuators may be utilized in conjunction with the present disclosure. For example, another form of powered actuator may include an arm structure (not shown) pivotally located alongside the conveyor 316. The arm structure may be constructed to be telescoping to increase and decrease in length. Moreover, the arm structure may be adapted to vertically raise and lower at the mounting end of the arm structure. Alternatively, a linear actuator may be connected to the distal or free end of the pivoting arm structure thereby to pick up temperature measuring devices 402 and insert the temperature measurement devices downwardly into selected sample food products.

Rather than inserting the temperature measurement devices 402 downwardly into selected food products, as shown in FIG. 13 temperature measurement devices 403 may be mounted on the conveyor 316 at selected locations on the conveyor. The device 403 may be of the same or similar construction as temperature measuring devices 402. The food products 14 are then placed over the mounted temperature measuring devices 403, which temperature measuring devices are capable of monitoring the temperature of the selected food products throughout the entire thermal processing of the sample food products as well as optionally during subsequent processing of the sample food products. The data from the temperature measurement devices 403 may be transmitted to the computing device 334 via wireless signal in the same manner as described above with respect to the temperature measuring devices 402, that are inserted downwardly into selected sample food products. It will be appreciated that by mounting the temperature measuring devices 403 directly onto the conveyor 316, the devices do not have to be retrieved or removed from the selected sample food products after thermal processing has been completed in the manner of devices 402 discussed above. Rather, the temperature sensing devices 403 remain with the conveyor and may be repeatedly used. Also, rather than utilizing a single probe, the temperature sensing devices 403 can be composed of multiple probes to accommodate for the possibility or likelihood that a probe may not be placed at the optimum location on a sample food product, for example, where the sample is the thickest.

Figure 10:
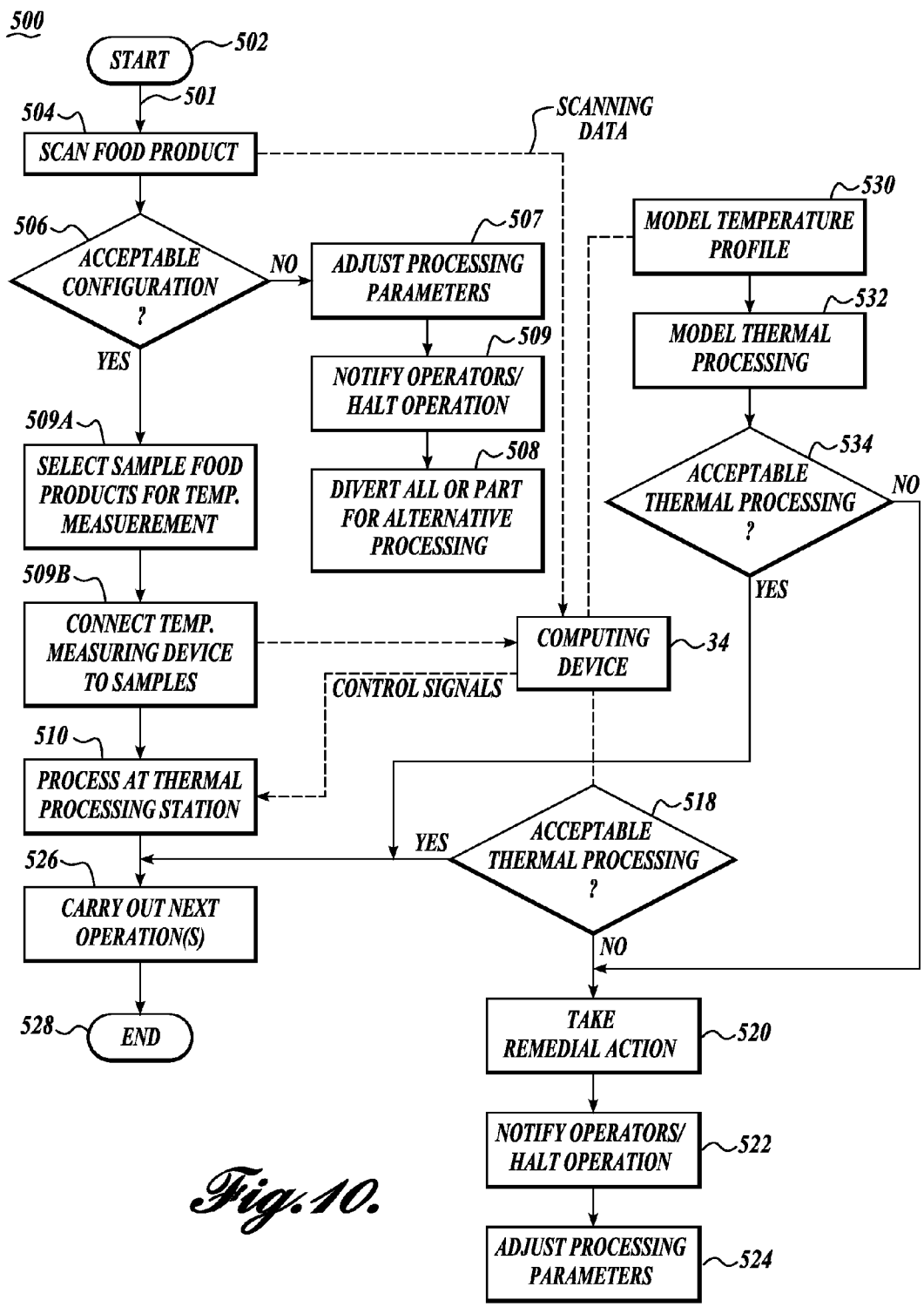
FIG. 10 is a flow diagram of one method of the present disclosure corresponding to the system of FIG. 9.

An overall method 500 in accordance with the present disclosure is illustrated in the flow chart of FIG. 10. The method starts at 502 and includes step 504 of scanning work pieces, for example food products, traveling along a product stream 501 towards a thermal processing station such as station 312 shown in FIG. 9. The food products are scanned, and the scanning data is used to determine physical attributes of the food products, including, for example, the volume, mass, thickness, centroid, area, texture, surface condition, and other physical features of the food products. The data from the scanning step is transmitted to the computing device 334 for processing and analysis of the scanning data. Based on the data received from the scanning step 504 and analysis of that data by the computing device 334, a determination is made at step 506 regarding whether the scanned food products are of acceptable configuration. If not, various actions can be taken at step 506 that are initiated by output signals from the computing device 334. As a first possibility, at step 507, the computing device may send operational signals to the thermal processing station 312 to alter process parameters at the thermal processing station, for example, as noted above, the humidity in the thermal processing station, the temperature of the heating/cooling medium used in the thermal processing station, and/or the level of air circulation within or through the thermal processing station. Also, the processing time on the food products in the thermal processing station may be altered. Signals may also be sent to other components of the thermal processing system 300 which have an effect on the processing of food products, for example, the speed at which the food products enter and travel through the food processing station.

As noted above, as an alternative to directly varying the process parameters of the thermal processing station or operational parameters at other locations of the system 300, the determination made at step 506 may instead cause the computing device at step 509 to send a notification to operational personnel that adjustments are required in the processing of food products due to significant problems existing at the thermal processing station or elsewhere in system 300. Notification of operational personnel can be via different means, including e-mail, telephone call, instant message, pager, horn or other audio signal, flashing lights, etc.

In addition to, or as an alternative to, sending notifications to operational personnel, the control system of the present disclosure may stop the processing of the food products, including shutting down the operation of the thermal processing station. Control specifications or limits can be set in advance so that a desired action(s) is/are taken depending on the extent of the deviation of the measured parameters or specifications of food products from a desired range or limit of parameters and specifications of the food products.

As a further option or possibility, at step 506, a decision can be made whether food products should continue along the product stream to the processing station 312, or be diverted for alternative processing or other purposes at step 508. This decision can be made based on the scanning data and analysis thereof. It may be that the scanning results indicate that specific food products are either too large, too thick, too thin, or of insufficient quality, etc., to be successfully processed at the thermal processing station 312. In that case, such food products that are not of acceptable configuration or composition can be diverted to alternative processing at step 508. This diversion option is typically feasible when a majority of the work pieces are within a desired specification but there are occasional outliers, perhaps if occasionally one food product is lying on top of another food product. By diverting the outliers, the remainder of the food products can continue on to being processed at station 312.

As a further possibility, rather than halting operation of the thermal processing station 312, it is possible to decide at step 506 (at least for a limited period of time) that all of the outer parameter food products from the main flow stream 501 be processed alternatively. Such diversion of the food products would require a diverting system that may be similar to diverter conveyor section 24 discussed above.

The scanning data from step 504 is also utilized to select sample food products for temperature measurement at step 509A. Such selection could be based on specific physical criteria, including, for example, the size, volume, and/or thickness of the food products scanned. Moreover, the scanning data may also be used to determine the location or locations on the selected sample food products at which to take temperature measurements.

In the next step 509B of the method 500, temperature measurement devices such as devices 402 are functionally connected to the selected sample food products. As discussed above, this can be carried out in an automated manner through the use of a robot or actuator that is able to pick up temperature measuring devices 402 and place the temperature measuring devices at a selected location or locations on the selected sample food products. Alternatively, as also discussed above, the temperature measurement devices 403 may be fixedly mounted on the conveyor 316. In this latter situation, selected sample food products are placed over the temperature sensing devices 403 such that the probes thereof engage into the food sample to the desired depth, typically at or very close to the center of the thickness of the food product.

The temperature sensing devices 402 or 403 travel along with the selected sample food products, including during thermal processing thereof at step 510. During the thermal processing of the selected food products, the temperature thereof is monitored. From such monitoring, it is determined whether or not the sample food product has been properly thermally processed, see step 518. As discussed above, this determination can be made by various methodologies. For example, if the methodology utilized is that the sample food product needs to reach a desired minimum temperature level, then that determination is readily made by monitoring the data signals from the temperature measurement devices. As discussed above, such minimum temperature level is typically set at a level at which the bacteria or pathogens in question are instantaneously killed. However, to ensure a desired confidence level that such minimum temperature is reached in all of the food products, typically the temperature selected is somewhat higher than the temperature needed to instantaneously kill the bacteria in question. The extent of the increase in the minimum temperature over the killing temperature can be dependent on the desired confidence level that all of the food products are properly thermally processed. Such confidence level may be up to, for example, three standard deviations from the nominal kill temperature.

As an alternative methodology, the temperature of the selected sample food products over time can be recorded to establish a temperature profile with the selected sample food products. Such temperature profile can be utilized to determine the level of reduction of the bacteria in question within the sample food product. Under governmental regulations, thermally processed food products are deemed to be safe if a particular reduction in the level of pathogens/bacteria in the food product can be achieved. Integration models can be used to determine the level of bacterial reduction achieved in the food product based on the temperature profile of the food product. It is possible to achieve the regulated required reduction in bacteria level without actually heating the food product to the level at which the bacteria in question is instantly killed.

Optionally, the temperature data from the temperature measurement devices 402 and 403 can be used to affect the operation of the thermal processing that occurs at step 510. The temperature monitoring data received by computing device 334 can be applied to control system algorithms, the results of which can be employed to control and/or adjust the operational parameters of the thermal processing station. Such parameters can include, for example, the processing time of the food products within the thermal processor, the humidity within the thermal processor, the temperature within the thermal processor, and/or the level of air flow within the thermal processor.

Step 518 depicts a decision of whether, based on the data from the temperature measuring devices, the food product is likely to have been acceptably thermally processed. If so, the food product continues on for the scheduled further processing. However, if the food product has not been acceptably thermally processed, then remedial action or measures are to be taken, see step 520. Such remedial actions can take many forms, including retaining the food products in the thermal processing unit for a further length of time for further processing. As an alternative, the affected food product may be diverted from the food product stream. In this regard, it will be necessary to divert the food product processed between the time of the last prior determination that the food product had been properly thermally processed to the next determination that the food product has been properly thermally processed. Other remedial actions include sanitizing, or confirming the sanitization of, any equipment in contact with the food products that are determined to not to have been properly thermally processed.

As an alternative to taking a remedial action in step 520, the determination at step 518, that the thermal processing of the food product was not acceptable can cause the computing device at step 522 to send a notification to operational personnel that adjustments are required in the thermal processing of the food products. As indicated above, notification can be carried out by many different means. In addition to, or as an alternative to, sending notifications to operational personnel, the computing device may send operational signals at step 524 to the thermal processing station 312 to alter process parameters at the thermal processing station. As mentioned above, such operational parameters can include the temperature within the thermal processing station, the humidity within the thermal processing station and/or the level of air circulation through the thermal processing station. Also, the processing time of the food products in the thermal processing station may be altered.

Rather than relying primarily on the temperature measurement from the temperature measuring devices 402 and 403, the thermal processing system 300 can be modeled at step 530 to predict the temperature profile of the food products, especially when being thermally processed within processing station 312. The modeled temperature profile of the food product can then be used to determine if the food product has been properly thermally processed at step 532. As discussed above, the methodologies that may be utilized in this regard can be the determination of whether or not the modeling indicates that the temperature within the food product has reached a minimum predetermined temperature, or if a sufficient level of the bacteria within the food product has been destroyed during thermal processing. The modeling of the temperature profile of the food product can take into consideration various factors that are specific to the food product and also specific to the configuration of processing system 300. Some of the factors specific to the food product include the type of food product, the thickness range of the food product, the initial temperature of the food product, the latent heat of the food product, the fat content of the food product, the moisture content of the food product, the loading level of the food product on the conveyance system. Factors pertaining to the thermal processing system 300 include, for example, the temperature of the pasteurization or heating medium within the processing station 312, the moisture level of the heating medium within the processing station 312, and/or the rate and volume of circulation of the heating medium within the processing station.

At step 534, if the modeling indicates that thermal processing of the food product has been properly carried out, then the food product simply continues on to the next processing step. However, if the modeling indicates that the food product has not been properly thermally processed, then one or more of the steps 520, 522, and 524, discussed above, may be undertaken.

Rather than utilizing all the foregoing conditions and factors in developing a temperature profile model, the system 300 can be operated under a process deviation control program that includes a real-time mathematical model that calculates the time and temperature required to achieve a desired bacterial kill level. Process parameter changes can be made, for example, to the temperature and/or humidity of the air within the processing station if sufficient deviations occur. The control program may utilize one or more proportional-integral-derivative (PID) controller algorithms which function to adjust one or more of the system parameters to seek to enable the system to still achieve a desired microbial kill rate even if one or more of the operational parameters of the system are beyond their preselected set point(s). For example, if the temperature in the processing station 312 deviates too far from the desired set point, the control system can not only seek to bring the temperature of the processing station 312 back to within a desired set point, but also can immediately decrease the speed of the conveyor 316 so that the food product dwell time in the processing station is increased. Also, the temperature in the processing station may be immediately increased and/or the flow rate of the air circulating within the processing station may be increased.

The modeling of system 300 can be used to verify the data from the temperature measuring devices 402 or 403. Moreover, if the model of the system 300, and the result of the temperature measuring devices satisfactorily correlate, then perhaps the number of temperature measuring devices required 402 or 403 per unit time may be decreased, which could reduce the operational cost of system 300.

Figure 11:
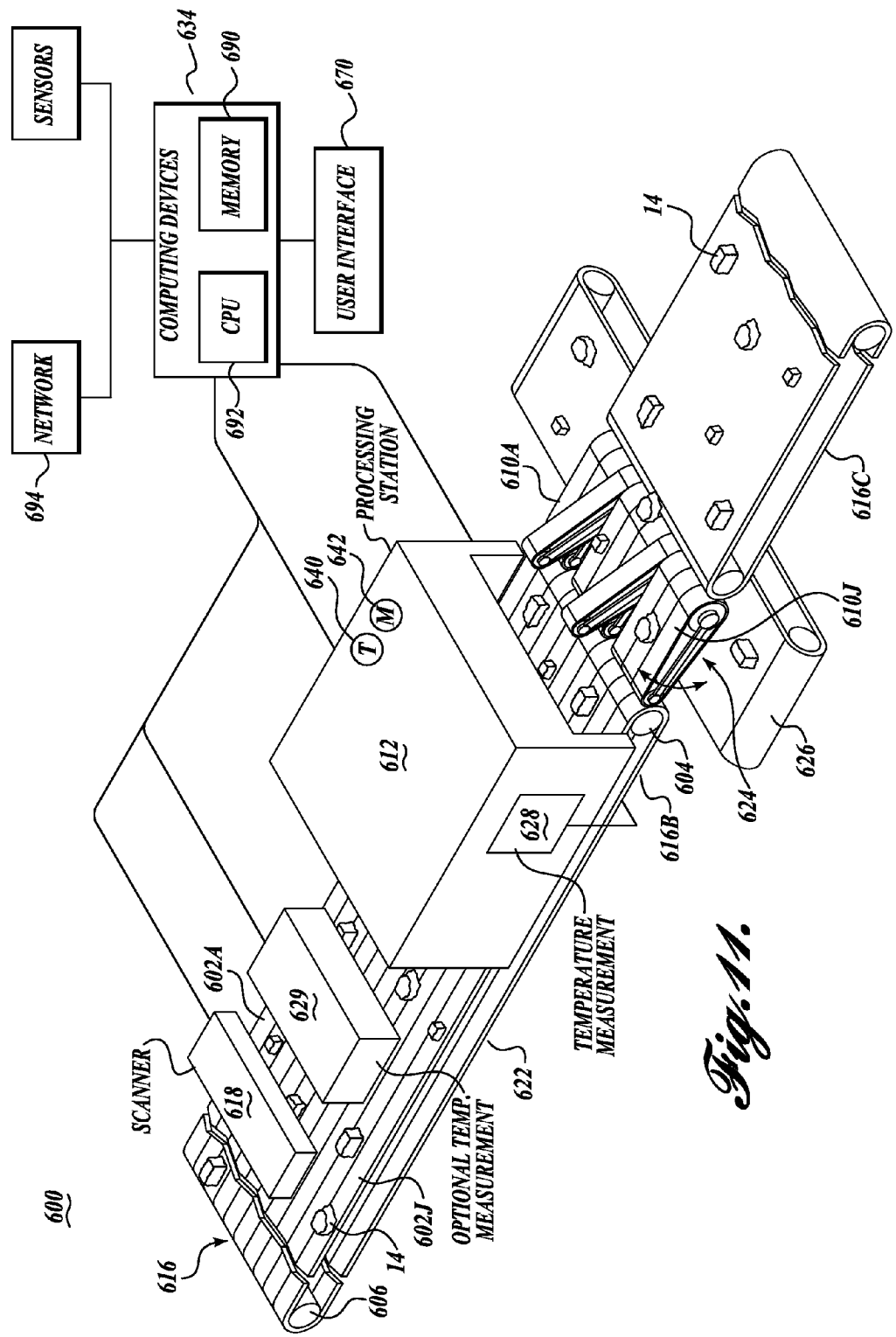
FIG. 11 is a schematic view of a further thermal measurement and process control system of the present disclosure.

FIG. 11 schematically illustrates a further temperature measurement and process control system 600 in accordance with the present disclosure. The aspects or components of system 600 that are the same or similar to system 10 are designated by the same part number as system 10 but in the 600 series. Those components of system 600 that correspond to the components described in systems 10 and 300 will not be described again with respect to system 600.

System 600 differs primarily from system 300 in that, in system 600 thermal measuring devices such as devices 402 and 403 are not utilized. Instead, the temperature of the food products is measured during the thermal processing of the food product, somewhat before completion of the thermal processing of the food product occurs. In this regard, as shown in FIG. 11, a temperature measurement station 628 is located within the thermal processing station 612. In this regard, high-speed temperature measurement devices may be inserted into the food product while within the thermal processing station 612 to measure the temperature of the food product. Typically, such temperature measurement would occur toward the latter part of the thermal processing of the food product since at that point the temperature of the food product would be increasing, whereas earlier on in the thermal processing of the food product, the temperature thereof may not have risen appreciably. From the temperature measurement of the food product within the thermal processing station, it is possible to ascertain to what extent the food product has been thermally processed and then calculate how much longer it would be necessary to process the food product to be successfully thermally processed. If such time required is predicted to be longer than the scheduled remaining duration of the food product within the processing station, the speed of the conveyor within the food processing station may be slowed or otherwise adjusted. As an alternative, the food product may be diverted to a further processing station using diverter conveyor station 624 positioned over transverse conveyor 626.

As an alternative to the foregoing, if from the temperature measurement taken within the processing station 612, it is determined that certain of the food products will require additional thermal processing beyond that to be carried out within the thermal processing station 612, such food products may continue on past the diverter conveyor section 624 and on to subsequent conveyor section 616C. A second thermal processing station, not shown, can be positioned in conjunction with conveyor section 616C for further processing of the food products that are determined to require such further processing. The second processing station may be designed to simply maintain the temperature of the food product for a sufficient length of time to achieve satisfactory thermal processing of the food product. If that is the case, such second thermal processing station may be of rather straightforward construction and design.

Continuing with the alternative, the food products that have been determined to be satisfactorily processed within thermal processing station 612 can be transferred on to transverse conveyor 626 via diverter conveyor section 624 for further normal processing of such food products.

As in systems 10 and 300 described above, the temperature measurements taken of the food products 14 can be utilized to adjust the operational parameters of the thermal processing station 612. For example, if a high incidence of incomplete thermal processing of the food products is occurring, then the temperature of the thermal processing station 612 may be required to be increased, and/or the speed of the conveyor 616 may need to be adjusted, and/or the moisture level within the thermal processing station 612 may need to be adjusted.

As also shown in FIG. 11, an optional temperature measurement station 628 may be positioned downstream of the scanner 618 and upstream of the thermal processing station 612. It may be helpful to measure the temperature of the food products entering the thermal processing station and such temperature information utilized to set or adjust the operational parameters of the thermal processing station 612. The temperature measurement methodology used at station 628 may employ infrared technology or other technology to determine not only the exterior temperature of the food product, but also the interior temperature of the food product.

As in temperature measurement and control systems 10 and 300 described above, the information from scanner 618 can be utilized to not only physically characterize the food products 14, but also used to adjust the operational parameters of the thermal processing station 612.

Further, as in systems 10 and 300, system 600 can also include the modeling of the system as well as the food product being processed by the system, thereby to predict the temperature profile of the food products being processed. From such temperature profile, the extent or level of thermal processing of the food products can be modeled. The results of such modeling can be utilized to verify the temperature measurements occurring within the thermal processing station 612. Also, the results of such modeling can be used to control the operation of system 600 including the operational parameters of thermal processing station 612.

It will be appreciated that the methods, systems and apparatus of the present invention can be used with workpieces and food products of a wide range of sizes from individual food portions or subportions to larger sized food products comprising multiple or many portions.

In this regard, a typical restaurant portion of chicken is about 100 grams and of a size of about 3.5 inches by 5.5 inches. One type of sub-portion may be chicken nuggets, which are typically from about 15 to 20 grams in weight. An example of a multiple portion food item is a pork belly that may range in weight for from about 5.5 to 20 pounds and have a thickness for from about 1.2 inches to 2.5 inches, a width of about 12 inches to 20 inches and length of about 22 inches to 36 inches. It is to be understood that these are examples of food products with which the present invention may be used, and are not intended to be inclusive of the sizes or types of work products with which the present invention may be used.

The invention claimed is:

1. A method of measuring the internal temperature of discrete food products thermally processed in a thermal processor while being conveyed by a conveyance system, comprising:
    (a) physically characterizing the food products being conveyed on the conveyance system;
    (b) based on the physical characterizing of the food products selecting sample food products for temperature measurement;
    (c) based on the physical characteristics of the selected sample food products, determining one or more locations on the selected sample food products that are expected to give a representative temperature at which to measure the internal temperature of the selected sample food products;
    (d) inserting temperature sensing devices into the selected sample food products at the selected locations using a powered insert apparatus and then retracting the powered insert apparatus away from the temperature sensing devices, the temperature sensing devices traveling with the selected sample food products on the conveyance system through the thermal processor as the food products are being processed; and
    (e) monitoring the temperatures sensed by the temperature sensing devices, including during the thermal processing of the selected sample food products.

2. The method of claim 1, wherein the food products are physically characterized by scanning of the food products.

3. The method of claim 1, wherein the temperature sensing devices are carried by the conveyance system and the selected sample food products are placed over the temperature sensing devices.

4. The method of claim 1, wherein the powered insert apparatus is selected from the group consisting of: (1) an actuator capable of moving relative to the conveyance system over the food products being carried by the conveyance system; (2) a multi-directional actuator capable of moving at least along, across, and diagonally relative to the conveyance system; and (3) a rotatable and extendable actuator positioned alongside the conveyance system and capable of rotating about a pivot axis relative to the conveyance system and simultaneously extending or retracting in length.

5. The method of claim 1, further comprising recording the data from the temperature sensing devices.

6. The method of claim 1, further comprising, based on the temperatures of the selected sample food products measured by the temperature sensing devices, controlling the operation of the thermal processor.

7. The method of claim 1, further comprising, based on the temperatures of the selected sample food products measured by the temperature sensing devices, determining the extent that the sample selected food products have been thermally processed.

8. The method of claim 7, wherein the level of thermal processing of the selected sample food products is determined by:
    (a) ascertaining if a threshold minimum temperature of the selected sample food products has been reached; and/or
    (b) determining the reduction in one or more selected bacteria resulting from the thermal processing of the selected sample food products.

9. The method of claim 7, wherein based on the determined level of thermal processing of the selected sample food products that has occurred, selecting the manner of the subsequent processing of the food products.

10. The method of claim 9, wherein the subsequent processing of the food products is determined depending on whether the thermal processing of the selected sample food products has been adequately satisfied, and if the thermal processing of the selected sample food products has been adequately satisfied, the food products are transmitted on for subsequent scheduled processing, and if the thermal processing of the selected sample food products has not been adequately satisfied, then taking remedial action.

11. The method of claim 10, wherein if the thermal processing of the selected sample food products has not been adequately performed, the remedial action comprises taking action with respect to at least one of the food products, conveyance system, and the thermal processor.

12. The method of claim 1, further comprising modeling of the temperature profile of the food products to determine the extent of the thermal processing in the food products and optionally to verify the measured temperatures of the selected sample food products.

13. The method of claim 12, wherein the modeling of the food products takes into consideration one or more factors selected from the group consisting of: the type of the food product, the density of the food product, the thickness range of the food product, initial temperature of the food product, the latent heat of the food product, the fat content of the food product, the moisture content of the food product, the loading level of the food product on the conveyance system, the speed of the conveyance system, the dwell time of the food product within the thermal processor, the level of power transmitted to the thermal processor, the temperature within the thermal processor, variations of temperature at different locations within the thermal processor, the moisture level of the heat transfer medium used within the thermal processor, the rate of air circulation within the thermal processor, the volume of air circulation within the thermal processor.

14. A method for processing a stream of food products in a thermal processing apparatus so that the food products have been sufficiently processed to meet regulatory requirements, comprising:
(a) scanning the food products to physically characterize the food products;
(b) based on the results of the scanning of the food products, selecting sample food products for temperature measurement;
(c) based on the results of the scanning of the food products, determining one or more locations of the selected sample food products expected to give a representative temperature of the food product at which to take temperature measurements;
(d) automatically functionally connecting temperature sensing devices with the selected sample food products using a powered connection device, the connection device being retracted away from the temperature sensing device, one temperature sensing device having been inserted into the same food product at the determined one or more optimal locations;
(e) monitoring the temperatures of the selected sample food products sensed by the temperature sensing devices including during thermal processing of the selected sample food products, the inserted temperature sensing devices traveling with the selected food products and the selected food products during thermal processing; and
(f) based on the monitored temperatures of the selected sample food products, determining if regulatory requirements for sufficient processing of the selected sample food products has occurred.

15. The method of claim 14, wherein automatically connecting the temperature sensing devices with the selected sample food products comprises automatically inserting the temperature sensing devices into the selected sample food products.

16. The method of claim 15, wherein the temperature sensing devices are automatically inserted into selected sample food products utilizing an actuating apparatus capable of moving relative to the stream of food products being conveyed.

17. The method of claim 14, wherein the automatic connecting of the temperature sensing devices with the selected sample food products comprises placing the selected sample food products on temperature sensing devices positioned on a conveyance system carrying the stream of food products.

18. The method of claim 14, wherein the thermal processing apparatus is operated under selected parameters based on the results of monitored temperatures of the selected sample food products adjusting the operational parameters of the thermal processing apparatus.

19. The method of claim 18, wherein the parameters under which the thermal processing apparatus is operated is selected from the group consisting of:
the time that the food products remain in the thermal processing apparatus;
the humidity of the atmosphere in the thermal processing apparatus;
the temperature of the heat transfer medium used in the thermal processing apparatus to thermally process the food products;
the volume of the food products within the thermal processing apparatus;
the mass of the food products within the thermal processing apparatus;
the air velocity throughout the thermal processing apparatus; and
the operation of a heating or cooling system used to heat or cool the heat transfer medium used in the thermal processing apparatus to thermally process the food products.

20. The method of claim 14, wherein the regulatory requirements that must be met for sufficient processing of the food products include achieving a minimum temperature throughout the entire volume of the food products or achieving a reduction in the presence of one or more specific bacteria in the food products.

21. The method of claim 14, wherein if the temperature measurement indicates that the thermal processing of the food products has not been satisfactorily completed, taking remedial steps with respect to the thermally processed food products.

22. The method of claim 21, wherein the remedial steps include one or more steps selected from the group consisting of:
(a) retaining the food product in the thermal processing apparatus for further thermal processing;
(b) diverting the food product from the food product stream;
(c) ensuring that the thermal processing apparatus is sanitized;
(d) further processing or reprocessing the affected food product; and (e) sanitizing equipment that has been in contact with a food product considered to be not properly processed.

23. The method of claim 14, further comprising predicting the temperature rise of the food products over time during thermal processing and from such predicted temperature rise determining the reduction in the level of selected bacteria during thermal processing of the food products.

24. The method of claim 23, further comprising controlling the operation of the thermal processing apparatus based on the predicted temperature rise in the selected food product and/or the determined reduction in the level of selected bacteria.

25. The method of claim 23, wherein predicting the temperature of the food product takes into consideration one or more factors selected from the group consisting of: the type of the food product, the density of the food product, the thickness range of the food product, initial temperature of the food product, the latent heat of the food product, the fat content of the food product, the moisture content of the food product, the loading level of the food product on a conveyance system, the speed of the conveyance system, the dwell time of the food product within the thermal processing apparatus, the level of power transmitted to the thermal processing apparatus, the temperature within the thermal processing apparatus, variations of temperature at different locations within the thermal processing apparatus, the moisture level of the heat transfer medium used within the thermal processing apparatus, the rate of air circulation within the thermal processing apparatus, and the volume of air circulation within the thermal processing apparatus.

26. The method of claim 14, further comprising recording the data from the temperature sensing devices.

27. A method for processing a stream of food products in a thermal processing apparatus so that the food products have been sufficiently processed to meet regulatory requirements, comprising:
(a) scanning the food products to physically characterize the food products prior to thermal processing of the food products;
(b) based on the results of the scanning of the food products predicting the temperature rise of the food products over time during the thermal processing and from such predicted temperature rise determining the reduction in the level of bacteria during thermal processing of the food products;
(c) based on the results of the scanning of the food products, selecting sample food products for temperature measurement;
(d) automatically functionally connecting temperature sensing devices with the selected sample food products;
(e) monitoring the temperatures of the selected sample food products sensed by the temperature sensing devices including during thermal processing of the selected sample food products; and
based on the monitored temperatures of the selected sample food products, determining if regulatory requirements for sufficient processing of the selected sample food products has occurred.

28. The method of claim 27, further comprising controlling the operation of the thermal processing apparatus based on the predicted temperature rise in the selected food product and/or the determined reduction in the level of selected bacteria.

29. The method of claim 27, wherein predicting the temperature of the food product takes into consideration one or more factors selected from the group consisting of: the type of the food product, the density of the food product, the thickness range of the food product, initial temperature of the food product, the latent heat of the food product, the fat content of the food product, the moisture content of the food product, the loading level of the food product on a conveyance system, the speed of the conveyance system, the dwell time of the food product within the thermal processing apparatus, the level of power transmitted to the thermal processing apparatus, the temperature within the thermal processing apparatus, variations of temperature at different locations within the thermal processing apparatus, the moisture level of the heat transfer medium used within the thermal processing apparatus, the rate of air circulation within the thermal processing apparatus, and the volume of air circulation within the thermal processing apparatus.

30. The method of claim 27, further comprising recording the data from the temperature sensing devices.

\* \* \* \* \*